United States Patent
Ciceri et al.

(10) Patent No.: US 11,013,698 B2
(45) Date of Patent: May 25, 2021

(54) COMBINATIONS OF LSD1 INHIBITORS FOR THE TREATMENT OF HEMATOLOGICAL MALIGNANCIES

(71) Applicant: Oryzon Genomics S.A., Madrid (ES)

(72) Inventors: Filippo Ciceri, Barcelona (ES); Serena Lunardi, Boston, MA (US); Tamara Maes, Castelldefels (ES); Cristina Mascaro Crusat, Barcelona (ES); Inigo Tirapu Fernandez De La Cuesta, Vienna (AT)

(73) Assignee: Oryzon Genomics S.A., Madrid (ES)

( * ) Notice: Subject to any disclaimer, the term of this patent is extended or adjusted under 35 U.S.C. 154(b) by 0 days.

(21) Appl. No.: 16/084,683

(22) PCT Filed: Mar. 13, 2017

(86) PCT No.: PCT/EP2017/055763
§ 371 (c)(1),
(2) Date: Sep. 13, 2018

(87) PCT Pub. No.: WO2017/157813
PCT Pub. Date: Sep. 21, 2017

(65) Prior Publication Data
US 2019/0083417 A1    Mar. 21, 2019

(30) Foreign Application Priority Data
Mar. 15, 2016 (EP) .................................. 16382117

(51) Int. Cl.
| | | |
|---|---|---|
| *A61K 31/05* | (2006.01) | |
| *A61K 31/12* | (2006.01) | |
| *A61P 35/02* | (2006.01) | |
| *A61K 31/135* | (2006.01) | |
| *A61K 31/17* | (2006.01) | |
| *A61K 31/203* | (2006.01) | |
| *A61K 31/282* | (2006.01) | |
| *A61K 31/015* | (2006.01) | |
| *A61K 31/337* | (2006.01) | |
| *A61K 31/4045* | (2006.01) | |
| *A61K 31/4745* | (2006.01) | |
| *A61K 31/475* | (2006.01) | |
| *A61K 31/519* | (2006.01) | |
| *A61K 31/555* | (2006.01) | |
| *A61K 31/704* | (2006.01) | |
| *A61K 31/7068* | (2006.01) | |
| *A61K 31/19* | (2006.01) | |
| *A61P 35/00* | (2006.01) | |
| *A61K 31/496* | (2006.01) | |

(Continued)

(52) U.S. Cl.
CPC ............ *A61K 31/015* (2013.01); *A61K 31/12* (2013.01); *A61K 31/135* (2013.01); *A61K 31/17* (2013.01); *A61K 31/19* (2013.01); *A61K 31/203* (2013.01); *A61K 31/282* (2013.01); *A61K 31/337* (2013.01); *A61K 31/4045* (2013.01); *A61K 31/475* (2013.01); *A61K 31/4745* (2013.01); *A61K 31/496* (2013.01); *A61K 31/519* (2013.01); *A61K 31/555* (2013.01); *A61K 31/64* (2013.01); *A61K 31/704* (2013.01); *A61K 31/7068* (2013.01); *A61K 33/36* (2013.01); *A61P 35/00* (2018.01); *A61P 35/02* (2018.01)

(58) Field of Classification Search
CPC .... A61K 31/015; A61K 31/12; A61K 31/135; A61K 31/17; A61K 31/19; A61K 31/203; A61K 31/282; A61K 31/337; A61K 31/4045; A61K 31/4745; A61K 31/475; A61K 31/496; A61K 31/519; A61K 31/555; A61K 31/64; A61K 31/704; A61K 31/7068; A61K 33/36; A61P 35/02; A61P 35/00
See application file for complete search history.

(56) References Cited

U.S. PATENT DOCUMENTS

| | | |
|---|---|---|
| 2,709,712 A | 5/1955 | Cawley et al. |
| 3,968,249 A | 7/1976 | Bernstein et al. |

(Continued)

FOREIGN PATENT DOCUMENTS

| | | |
|---|---|---|
| EP | 1704859 | 9/2006 |
| JP | 10152462 | 6/1998 |

(Continued)

OTHER PUBLICATIONS

International Search Report of International Application No. PCT/EP/2017/055763, dated Jun. 12, 2017.

(Continued)

*Primary Examiner* — Kortney L. Klinkel
*Assistant Examiner* — William Y Lee
(74) *Attorney, Agent, or Firm* — Finnegan, Henderson, Farabow, Garrett & Dunner, LLP

(57) ABSTRACT

The instant invention relates to combinations of the compound of formula (I) or pharmaceutically acceptable salts thereof with other active pharmaceutical ingredients

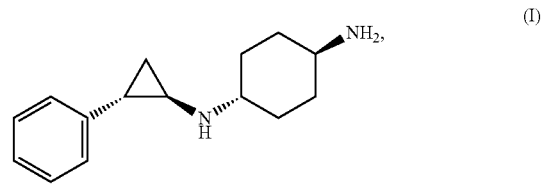

pharmaceutical compositions comprising them, and their use as medicaments, particularly for the treatment of hematological malignancies.

18 Claims, 24 Drawing Sheets

(51) Int. Cl.
*A61K 33/36* (2006.01)
*A61K 31/64* (2006.01)

(56) References Cited

U.S. PATENT DOCUMENTS

| | | | |
|---|---|---|---|
| 5,712,274 | A | 1/1998 | Sueoka et al. |
| 8,524,717 | B2 | 9/2013 | Guibourt et al. |
| 8,722,743 | B2 | 5/2014 | Ortega-Munoz et al. |
| 8,859,555 | B2 | 10/2014 | Ortega Muñoz et al. |
| 8,946,296 | B2 | 2/2015 | Ortega Muñoz et al. |
| 8,993,808 | B2 | 3/2015 | Guibourt et al. |
| 9,006,449 | B2 | 4/2015 | Fyfe et al. |
| 9,061,966 | B2 | 6/2015 | Laria et al. |
| 9,149,447 | B2 | 10/2015 | Ortega Muñoz et al. |
| 9,181,198 | B2 | 11/2015 | Ortega Muñoz et al. |
| 9,186,337 | B2 | 11/2015 | Baker et al. |
| 9,469,597 | B2 | 10/2016 | Ortega Muñoz et al. |
| 9,487,512 | B2 | 11/2016 | Ortega Muñoz et al. |
| 9,616,058 | B2 | 4/2017 | Cesar Castro Palomino Laria et al. |
| 9,670,136 | B2 | 6/2017 | Ortega Muñoz et al. |
| 9,676,701 | B2 | 6/2017 | Fyfe et al. |
| 9,708,309 | B2 | 7/2017 | Ortega Muñoz et al. |
| 9,790,196 | B2 | 10/2017 | Baker et al. |
| 9,908,859 | B2 | 3/2018 | Baker et al. |
| 9,944,601 | B2 | 4/2018 | Ortega Muñoz et al. |
| 10,202,330 | B2 | 2/2019 | Ortega Muñoz et al. |
| 10,214,477 | B2 | 2/2019 | Ortega Muñoz et al. |
| 10,221,125 | B2 | 3/2019 | Diodone et al. |
| 10,233,178 | B2 | 3/2019 | Ortega Muñoz et al. |
| 10,265,279 | B2 | 3/2019 | De mario et al. |
| 10,329,256 | B2 | 6/2019 | Ortega Muñoz et al. |
| 10,780,081 | B2 | 9/2020 | Maes et al. |
| 2005/0282803 | A1 | 12/2005 | Haley et al. |
| 2007/0027135 | A1 | 2/2007 | Bruncko et al. |
| 2008/0139665 | A1 | 6/2008 | Schuele et al. |
| 2010/0324147 | A1 | 12/2010 | McCafferty et al. |
| 2011/0312896 | A1 | 12/2011 | Distelhorst et al. |
| 2013/0137650 | A1 | 5/2013 | Armstrong et al. |
| 2014/0212414 | A1 | 7/2014 | Oh et al. |
| 2014/0296255 | A1 | 10/2014 | Maes et al. |
| 2014/0329833 | A1 | 11/2014 | Maes et al. |
| 2015/0174138 | A1 | 6/2015 | Bernstein et al. |
| 2016/0000768 | A1 | 1/2016 | Castro-Palomino Laria et al. |
| 2016/0045456 | A1 | 2/2016 | Guibourt et al. |
| 2016/0081947 | A1 | 3/2016 | Maes et al. |
| 2017/0209432 | A1 | 7/2017 | Fyfe et al. |
| 2017/0281566 | A1 | 10/2017 | Ciceri et al. |
| 2018/0284095 | A1 | 10/2018 | Maes et al. |
| 2019/0085372 | A1 | 3/2019 | Carceller González et al. |
| 2019/0153538 | A1 | 5/2019 | Cheng et al. |
| 2019/0256929 | A1 | 8/2019 | Birzele et al. |
| 2019/0256930 | A1 | 8/2019 | Arévalo et al. |

FOREIGN PATENT DOCUMENTS

| | | |
|---|---|---|
| RU | 2341283 C2 | 12/2008 |
| WO | WO93/07148 | 4/1993 |
| WO | WO2002/22577 | 3/2002 |
| WO | WO2004/080421 | 9/2004 |
| WO | WO2004/106328 | 12/2004 |
| WO | WO2005/049594 | 6/2005 |
| WO | WO2006/071608 | 7/2006 |
| WO | WO2006/087206 | 8/2006 |
| WO | WO2007/021839 | 7/2007 |
| WO | WO2007/109120 | 9/2007 |
| WO | WO2008/127734 | 10/2008 |
| WO | WO2009/040517 | 4/2009 |
| WO | WO2010/011845 | 1/2010 |
| WO | WO2010/043721 | 4/2010 |
| WO | WO2010/084160 | 7/2010 |
| WO | WO2010/138588 | 12/2010 |
| WO | WO2010/139784 | 12/2010 |
| WO | WO2010/143582 | 12/2010 |
| WO | WO2011/022489 | 2/2011 |
| WO | WO2011/035941 | 3/2011 |
| WO | WO2011/042217 | 4/2011 |
| WO | WO2011/054843 | 5/2011 |
| WO | WO2011/091213 | 7/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2011/143651 | 11/2011 |
| WO | WO2012/013727 | 2/2012 |
| WO | WO2012/013728 | 2/2012 |
| WO | WO2012/034116 | 3/2012 |
| WO | WO2012/042042 | 4/2012 |
| WO | WO2012/045883 | 4/2012 |
| WO | WO2012/072713 | 6/2012 |
| WO | WO2012/075381 | 6/2012 |
| WO | WO2012/107498 | 8/2012 |
| WO | WO2012/107499 | 8/2012 |
| WO | WO2012/116170 | 8/2012 |
| WO | WO2012/135113 | 10/2012 |
| WO | WO2012/156531 | 11/2012 |
| WO | WO2012/156537 | 11/2012 |
| WO | WO 2013/07322 A1 | 4/2013 |
| WO | WO2013/057320 | 4/2013 |
| WO | WO2014/134583 | 9/2014 |
| WO | WO2015/70020 | 5/2015 |
| WO | WO2015/116740 | 8/2015 |
| WO | WO2016/177656 | 11/2016 |
| WO | WO2016/198649 | 12/2016 |
| WO | WO2017/013061 | 1/2017 |
| WO | WO2017/060319 | 4/2017 |
| WO | WO2017/157825 | 9/2017 |
| WO | WO2017/158136 | 9/2017 |
| WO | WO2017/212061 | 12/2017 |
| WO | WO2018/083138 | 5/2018 |
| WO | WO2018/083189 | 5/2018 |
| WO | WO2019/025588 | 2/2019 |
| WO | WO2019/211491 | 11/2019 |
| WO | WO2020/188089 | 9/2020 |
| WO | WO2020/188090 | 9/2020 |
| WO | WO2020/193631 | 10/2020 |

OTHER PUBLICATIONS

Written Opinion of the International Search Authority of International Application No. PCT/EP/2017/055763.
Al-Nasiry et al "The use of Alamar Blue assays for quantitative analysis of viability, migration and invasion of choriocarcinoma cells", Human Reproduction, 22(5):1304-1309, 2007.
Barlesi et al, "Global histone modifications predict prognosis of resected non small-cell lung cancer",J Clin Oncol,2007,25, 4358-4364.
Benelkebir et al, "Enantioselective synthesis of tranylcypromine analogues as lysine demethylase (LSD1) inhibitors", Bioorg Med Chem, 2011,19(12),3709-3716.
Binda et al, "Biochemical, structural, and biological evaluation of tranylcypromine derivatives as inhibitors of histone demethylases LSD1 and LSD2", J Am Chem Soc,2010,132(19),6827-6833.
Cahn et al, "Specification of Molecular chirality", Angewandte Chemie International Edition in English, 5(4):385-415, 1966.
Choi et al "Histone demethylase LSD1 is required to induce skeletal muscle differentiation by regulating myogenic factors" (2010) Biochemical and Biophysical Research Communications 401(3), 327-332.
Chou et al, Analysis of combined drug effects: a new look at a very old problem. Trends in Pharmacological Sciences, 450-454, 1983.
Chou, "Drug combination studies and their synergy quantification using the Chou-Talalay method". Cancer Research, 70(2):440-446, 2010.
Chou, "Theoretical basis, experimental design, and computerized simulation of synergism and antagonism in drug combination studies", Pharmacological Reviews, 58(3):621-681, 2006.
Chu et al, "A proposed mechanism of action of 1-beta-D-arabinofuranosyl-cytosine as an inhibitor of the growth of leukemic cells", Biochemical Pharmacology, 11:423-430, 1962.

(56) References Cited

OTHER PUBLICATIONS

Culhane et al, A mechanism-based inactivator for histone demethylase LSD1, J Am Chem Soc, 2006, 128(14), 4536-4537.
Culhane et al, "Comparative analysis of small molecules and histone substrate analogues as LSD1 lysine demethylase inhibitors", J Am Chem Soc, 2010,132(9),3164-3176.
Daigle et al, "Selective killing of mixed lineage leukemia cells by a potent small molecule DOT1L inhibitor". Cancer Cell, 20:53-65, 2011.
Di Stefano et al, Mutation of *Drosophila* Lsd1 disrupts H3-K4 methylation, resulting in tissue-specific defects during development, Curr Biol,2007, 17(9), 808-12.
Elsheikh et al "Global histone modifications in breast cancer correlate with tumor phenotypes, prognostic factors and patient outcome", Canc Res, 2009,69, 3802-3809.
Feng et al, "Pharmacological inhibition of LSD1 for the treatment of MLL-rearranged leukemia", Journal Hematology & Oncology, 2016, 9:24.
Fischer et al, "Recovery of learning and memory is associated with chromatin remodelling", Nature, 2007,447, 178-182.
Forneris et al "LSD1: oxidative chemistry for multifaceted functions in chromatin Regulation." Trends in Biochemical Sciences 2008,33(4), 181-189.
Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.
Han et al, "Synergistic reactivation of epigenetically silenced genes by combinatorial inhibition of DNMTs and LSD1 in cancer cells", PloS One, 2013, 8(9), e75136.
Hayami et al, "Overexpression of LSD1 contributes to human carcinogenesis through chromatin regulation in various cancers", Int J Cancer, 2011, 128(3), 574-86.
Huang et al, "Novel oligoamine analogues inhibit lysine-specific demethylase 1 (LSD1) and induce re-expression of epigeneticall silenced genes",Clin Cancer Res,2009, 15(23), 7217-28.
Huang et al, "p53 is regulated by the lysine demethylase LSD1",Nature,2007,449, 105-108.
Huang et al,"Inhibition of lysine-specific demethylase 1 by polyamine analogues results in reexpression of aberrantly silenced genes", PNAS,2007, 104(19), 8023-8028.
Huls et al, "Azacitidine in AML: a treatment option?", Blood, 126(3):283-284, 2015.
Kahl et al,"Androgen receptor coactivators lysine-specific histone demethylase 1 and four and a half LIM domain protein 2 predict risk of prostate cancer recurrence", Cancer Res,2006,66 (23), 11341-11347.
Lan et al "Mechanisms involved in the regulation of histone lysine demethylases". Current Opinion in Cell Biology, 2008,20, 316-325.
Lee et al, "Histone H3 lysine 4 demethylation is a target of nonselective antidepressive medications",Chem Biol, 2006,13(6), 563-567.
Liang et al, "Inhibition of the histone demethylase LSD1 blocks alpha-herpesvirus lytic replication and reactivation from latency",Nat Med, 2009,15 (11), 1312-1317.
Lim et al, "Lysine-specific demethylase 1 (LSD1) is highly expressed in ER-negative breast cancers and a biomarker predicting aggressive biology", Carcinogenesis,2010, 31(3), 512-20.
Maskovskij M.D., Lekarstvennye sredstva, B 2 t., T.1—M.: OOO, "Izdatel'stvo Novaâ Volna", 2001, 540, p. 11.
Metzger et al, "LSD1 demethylates repressive histone marks to promote androgen-receptor-dependent transcription",Nature,2005, 437(7057),436-9.
Mimasu et al "Crystal structure of histone demethylase LSD1 and tranylcypromine at 2.25 Å" Biochemical and Biophysical Research Communications ,2008,366, 15-22.
Mimasu et al, "Structurally designed trans-2-phenylcyclopropylamine derivatives potently inhibit histone demethylase LSD1/KDM1", Biochemistry,2010,49(30), 6494-6503.

Neelamegan et al, "Brain-penetrant LSD1 inhibitors can block memory consolidation", ACS Chem Neurosci, 2012, 3(2), 120-128.
Ogasawara et al, "Synthesis and biological activity of optically active NCL-1, a lysine-specific demethylase 1 selective inhibitor",Bioorg Med Chem, 2011, doi:10.1016/j.bmc.2010.12.024.
Pollock et al, Lysine-specific histone demethylase 1 inhibitors control breast cancer proliferation in ERalpha-dependent and -independent manners, ACS Chem Biol 2012,7,1221-1231.
Prusevich et al, "A selective phenelzine analogue inhibitor of histone demethylase LSD1", ACS Chem Biol, 2014, 9(6):1284-1293.
Reddy et al, "Role of lysine-specific demethylase 1 in the proinflammatory phenotype of vascular smooth muscle cells of diabetic mice",Circ Res,2008,103, 615-23.
Sato et al, "Improving specificity of epigenetic therapy through combined targeting of DNA and histone methylation", Eur Journal of Cancer, vol. 50, supl 6, 192, 2014.
Schmidt et al,"trans-2-phenylcyclopropylamine is a mechanism-based inactivator of the histone demethylase LSD1", Biochemistry, 2007,46(14),4408-4416.
Schulte et al, "Lysine-specific demethylase 1 is strongly expressed in poorly differentiated neuroblastoma: implications for therapy", Cancer Res,2009,69(5),2065-71.
Scoumanne et al "Protein methylation: a new mechanism of p53 tumor suppressor regulation" Histol Histopathol 2008,23, 1143-1149.
Scoumanne et al, "The lysine-specific demethylase 1 is required for cell proliferation in both p53-dependent and -independent manners", J Biol Chem, 2007,282(21), 15471-5.
Seligson et al, "Global histone modification patterns predict risk of prostate cancer recurrence",Nature, 2005,435, 1262-1266.
Seligson et al,"Global levels of histone modifications predict prognosis in different cancers" ,Am J Path, 2009,174,1619-28.
Sharma et al, "(Bis)urea and (bis)thiourea inhibitors of lysine-specific demethylase 1 as epigenetic modulators", J Med Chem, 2010,53(14), 5197-5212.
Shi et al,"Histone demethylation mediated by the nuclear amine oxidase homolog LSD1", Cell, 2004,119,941-953.
Shi, "Histone lysine demethylases: emerging roles in development, physiology and disease", Nature Reviews Genetics 2007, 8:829-833.
Szewczuk et al, "Mechanistic analysis of a suicide inactivator of histone demethylase LSD1", Biochemistry, 2007,46, 6892-6902.
Ueda et al, "Identification of cell-active lysine specific demethylase 1-selective inhibitors",J Am Chem Soc, 2009,131(48), 17536-17537.
Vengerovsky, "Pharmacological incompatibility", Bulletin of Siberian Medicine, 2003, 3, 49-56.
Wang et al, "Novel histone demethylase LSD1 inhibitors selectively target cancer cells with pluripotent stem cell properties," Cancer Research, 2011, 71(23):7238-49.
Wang et al "LSD1 Is a Subunit of the NuRD Complex and Targets the Metastasis Programs in Breast Cancer" Cell 2009, 138, 660-672.
Wang et al, "The lysine demethylase LSD1 (KDM1) is required for maintenance of global DNA methylation", Nature Genetics, 2009, 41(1), 125-129.
WHO Drug Information, 23(1):1-25, 2009.
WHO Drug Information, 25(3):219-294, 2011.
WHO Drug Information, 28(1):1-70, 2014.
WHO Drug Information, 28(4):423-484, 2014.
WHO Drug Information, Recommended INN List 56, 20(3):163-235, 2006.
Wolfrom et al, "Halogen and nucleoside derivatives of acyclic 2-amino-2-deoxy-D-glucose", Journal of Organic Chemistry, 29(11):3280-3283, 1964.
Yang et al "Structural Basis for the Inhibition of the LSD1 Histone Demethylase by the Antidepressant trans-2-Phenylcyclopropylamine" Biochemistry 2007,46 (27), 8058-8065.
Yang et al "Structural basis of histone demethylation by LSD1 revealed by suicide inactivation" Nature Structural & Molecular Biology 2007, 14(6), 535-539.

(56) References Cited

OTHER PUBLICATIONS

Yu et al, "Catalytic site remodeling of the DOT1L methyltransferase by selective inhibitors", Nature Communications 3(1288):1-11, 2012.
Johnson et al, CAPLUS, Document No. 157:576967, "Preparation of cyclopropylamines as LSD1 inhibitors in the treatment of cancer", 2012.
Co-pending U.S. Appl. No. 16/085,024, filed Sep. 14, 2018.
Co-pending U.S. Appl. No. 16/346,915, filed Dec. 11, 2019.
Co-pending U.S. Appl. No. 16/635,704, filed Jan. 31, 2020.
Co-pending U.S. Appl. No. 16/859,061, filed Apr. 27, 2020.
Co-pending U.S. Appl. No. 16/859,048, filed Apr. 27, 2020.
Co-pending U.S. Appl. No. 16/856,312, filed Apr. 23, 2020.
Co-pending U.S. Appl. No. 16/869,948, filed May 8, 2020.
Co-pending U.S. Appl. No. 16/881,171, filed May 22, 2020.
Co-pending U.S. Appl. No. 16/893,528, filed Jun. 5, 2020.
Co-pending U.S. Appl. No. 16/893,553, filed Jun. 5, 2020.
Co-pending U.S. Appl. No. 16/910,415, filed Jun. 24, 2020.
Co-pending U.S. Appl. No. 16/990,054, filed Aug. 11, 2020.
Gallipoli, Paolo et al., "Epigenetic regulators as promising therapeutic targets in acute myeloid Leukemia," Ther. Adv. Hematol., vol. 6, No. 3, pp. 103-119 (2015).
Ramirez, Lorimar M.D., et al., "HDAC and LSD1 Inhibitors Synergize to Induce Cell Death in Acute Leukemia Cells," Molecular Pharmacology, Drug Resistance: Poster I, vol. 118, issue 21, pp. 1-2, Nov. 13, 2011.

MV(4;11) (n=2)

MOLM-13 (n=2)

MV(4;11) (n=1)

OCI-AML3 (n=2)

MOLM-13 (n=2)

MV(4;11) (n=2)

MOLM-13 (n=2)

MV(4;11) (n=2)

MOLM-13 (n=1)

MV(4;11) (n=2)

OCI-AML3 (n=2)

MOLM-13 (n=2)

MV(4;11) (n=2)

MOLM-13 (n=2)

MV(4;11) (n=2)

MOLM-13 (n=2)

MV(4;11) (n=2)

MOLM-13 (n=2)

MV(4;11) (n=2)

MOLM-13 (n=1)

MOLM-13 (n=2)

MV(4;11) (n=1)

MV(4;11) (n=3)

MOLT-4 (n=2)

MOLT-4 (n=2)

MOLT-4 (n=1)

MOLT-4 (n=2)

MOLT-4 (n=2)

MOLT-4 (n=1)

MOLT-4 (n=2)

COMBINATIONS OF LSD1 INHIBITORS FOR THE TREATMENT OF HEMATOLOGICAL MALIGNANCIES

This application is a national stage filing under 35 U.S.C. § 371 of International Application No. PCT/EP2017/055763, filed on Mar. 13, 2017, which claims priority of European Patent Application No. 16382117.6, filed Mar. 15, 2016. The contents of these applications are each incorporated herein by reference.

FIELD OF THE INVENTION

The instant invention relates to combinations of LSD1 inhibitors, particularly of ORY-1001 with other anticancer agents. The combinations are particularly useful for the treatment of hematological malignancies.

BACKGROUND OF THE INVENTION

Aberrant gene expression in affected tissue as compared to normal tissue is a common characteristic of many human diseases, including cancer. Gene expression patterns are controlled at multiple levels in the cell. Control of gene expression can occur through modifications of DNA: DNA promoter methylation is associated with suppression of gene expression. Several inhibitors of DNA methylation are approved for clinical use including the blockbuster Vidaza™. Another class of modifications involve histones which form the protein scaffold that DNA is normally associated with (coiled around) in eukaryotic cells. Histones play a crucial role in organizing DNA and the regulated coiling and uncoiling of DNA around the histones is critical in controlling gene expression—coiled DNA is typically not accessible for gene transcription. A number of histone modifications have been discovered including histone acetylation, histone lysine methylation, histone arginine methylation, histone ubiquinylation, and histone sumoylation, many of which modify accessibility to the associated DNA by the cells transcriptional machinery. These histone marks serve to recruit various protein complexes involved in transcription and repression. An increasing number of studies are painting an intricate picture of how various combinations of histone marks control gene expression in cell-type specific manner and a new term has been coined to capture this concept: the histone code.

The prototypical histone mark is histone acetylation. Histone acetyl transferase and histone deacetylases are the catalytic machines involved in modulation of this histone mark although typically these enzymes are parts of multi-protein complexes containing other proteins involved in reading and modifying histone marks. The components of these protein complexes are typically cell-type specific and typically comprise transcriptional regulators, repressors, co-repressors, receptors associated with gene expression modulation (e.g., estrogen or androgen receptor). Histone deacetylase inhibitors alter the histone acetylation profile of chromatin. Accordingly, histone deacetylase inhibitors like Vorinostat (SAHA), Trichostatin A (TSA), and many others have been shown to alter gene expression in various in vitro and in vivo animal models. Clinically, histone deacetylase inhibitors have demonstrated activity in the cancer setting and are being investigated for oncology indications as well as for neurological conditions and other diseases.

Another modification that is involved in regulating gene expression is histone methylation including lysine and arginine methylation. The methylation status of histone lysines has recently been shown to be important in dynamically regulating gene expression.

A group of enzymes known as histone lysine methyl transferases and histone lysine demethylases are involved in histone lysine modifications. One particular human histone lysine demethylase enzyme called Lysine Specific Demethylase-1 (LSD1) was recently discovered[1] to be involved in this crucial histone modification. LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds. LSD1 has been recognized as an interesting target for the development of new drugs to treat cancer, neurological diseases and other conditions.

Cyclopropylamine containing compounds are known to inhibit a number of medically important targets including amine oxidases like Monoamine Oxidase A (MAO-A; or MAOA), Monoamine Oxidase B (MAO-B; or MAOB), and Lysine Specific Demethylase-1 (LSD1). Tranylcypromine (also known as 2-phenylcyclopropylamine), which is the active ingredient of Parnate® and one of the best known examples of a cyclopropylamine, is known to inhibit all of these enzymes. Since MAO-A inhibition may cause undesired side effects, it would be desirable to identify cyclopropylamine derivatives that exhibit potent LSD1 inhibitory activity while being devoid of or having substantially reduced MAO-A inhibitory activity.

In view of the lack of adequate treatments for conditions such as cancer, there is a desperate need for disease modifying drugs and drugs that work by inhibiting novel targets. There is thus a need for improved methods and compositions that can be used to treat hyperproliferative diseases, particularly hematological malignancies.

International Patent Application WO 2013/057322[2] discloses a number of LSD1 inhibitors, including the compound of formula (I):

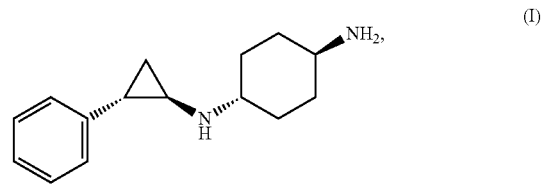 [SMILES: N[C@H]1CC[C@H](N[C@@H]2C[C@H]2c2ccccc2)CC1]

also known as ORY-1001 or (trans)-N1-((1R,2S)-2-phenyl-cyclopropyl)cyclohexane-1,4-diamine.

SUMMARY OF THE INVENTION

The invention is based at least in part upon the discovery that additive or synergistic effects in inhibiting the growth of cancer cells can be achieved by administering the compound of formula (I), or a pharmaceutically acceptable salt thereof, in combination with certain other specific agents. The combination and methods may be useful in the treatment of hyperproliferative disorders, particularly hematological malignancies.

The instant invention relates to combinations of LSD1 inhibitors, particularly of the compound of formula (I) or a pharmaceutically acceptable salt thereof

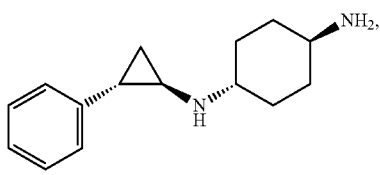
(I)

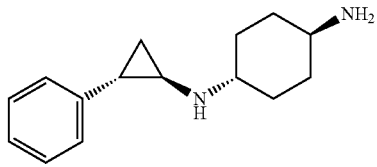
(I)

with one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof.

Accordingly, the present invention provides a combination comprising a compound of formula (I):

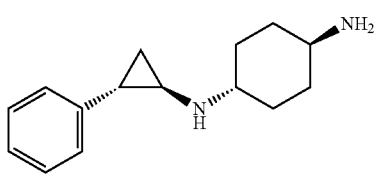
(I)

or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof.

In another aspect, the present invention is directed to a combination comprising a compound of formula (I):

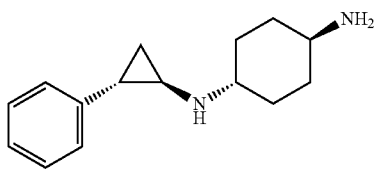
(I)

or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof, for use in the treatment of a hyperproliferative disorder, particularly a hematological malignancy, including myeloid hematological malignancies and lymphoid hematological malignancies, e.g. as described in more detail below.

In another aspect, the present invention is directed to a method for treating a hyperproliferative disorder, particularly a hematological malignancy, in a patient in need thereof, comprising administering to said patient a therapeutically effective amount of a compound of formula (I):

or a pharmaceutically acceptable salt thereof, and a therapeutically effective amount of one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof. In certain embodiments, said hematological malignancy is a myeloid hematological malignancy. In certain embodiments, said hematological malignancy is a lymphoid hematological malignancy.

In another aspect, the present invention is directed to a method for treating a hyperproliferative disorder, particularly a hematological malignancy, in a patient in need thereof, comprising administering to said patient a therapeutically effective amount of combination comprising a compound of formula (I):

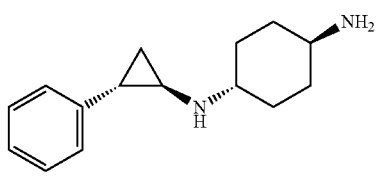
(I)

or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof. In certain embodiments, said hematological malignancy is a myeloid hematological malignancy. In certain embodiments, said hematological malignancy is a lymphoid hematological malignancy.

In another aspect, the present invention is directed to a method for treating a hyperproliferative disorder, particularly a hematological malignancy, in a patient in need thereof, comprising administering to said patient a pharmaceutical composition comprising a compound of formula (I):

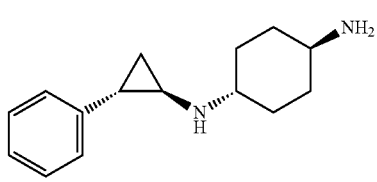
(I)

or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof, and one or more pharmaceutically acceptable excipients. In certain embodiments, said hematological malignancy is a myeloid hematological malignancy. In certain embodiments, said hematological malignancy is a lymphoid hematological malignancy.

In another aspect, the present invention provides a pharmaceutical composition comprising a compound of formula (I):

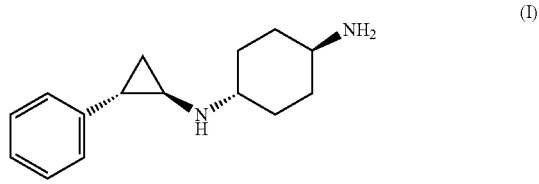 [SMILES: N[C@H]1CC[C@H](N[C@@H]2C[C@H]2c2ccccc2)CC1]

(I)

or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof, and one or more pharmaceutically acceptable excipients.

DETAILED DESCRIPTION OF THE INVENTION

Figure 1:
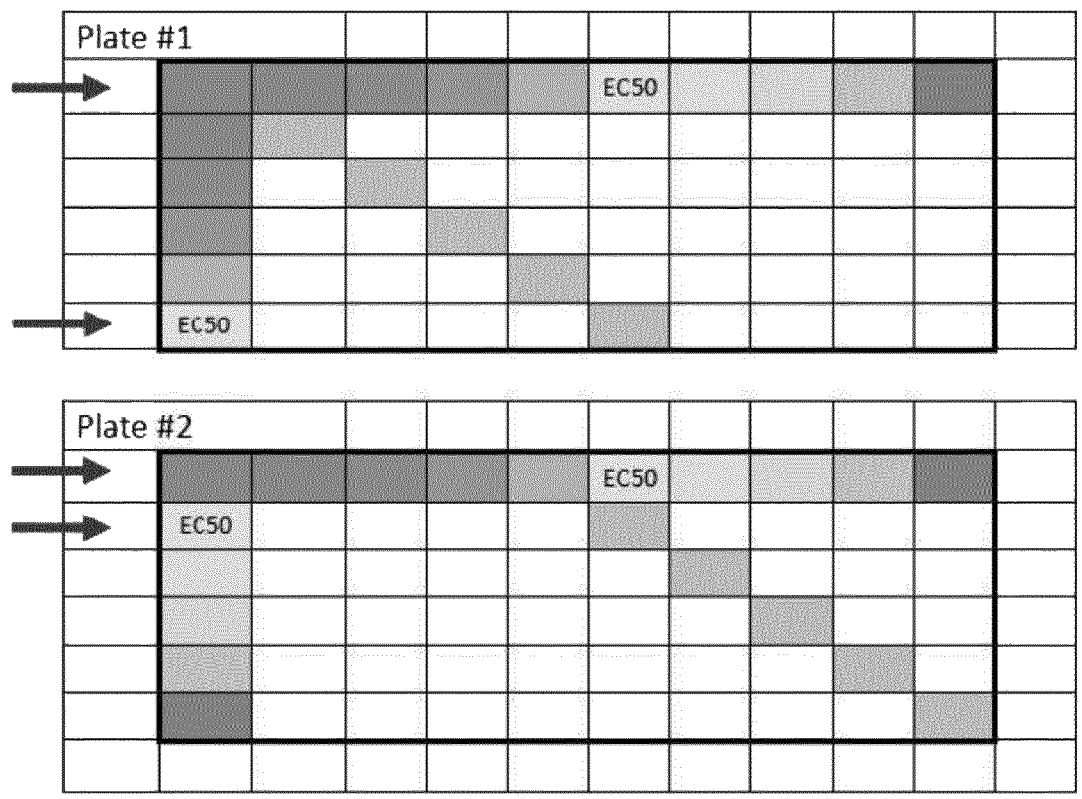
FIG. 1: Plate organization for 9×9 matrix assays used in Examples 1 and 2.

The present invention is based upon the discovery that the compound of formula (I), or a pharmaceutically acceptable salt thereof, and other therapeutic agents, as described herein, can be used in combination to treat hematological malignancies, with superior results than those attained by treatment with the compound of formula (I) alone or the other therapeutic agent alone.

In detail, the present invention provides a combination comprising the compound of formula (I), or a pharmaceutically acceptable salt thereof, and one or more therapeutic agents selected from a retinoic acid analogue, a nucleoside analogue, a DOT1L inhibitor, a HDAC inhibitor, a demethylating agent, an FLT3 inhibitor, a BCL2 inhibitor, an MDM2 inhibitor, a c-KIT inhibitor, a BET inhibitor, an anthracycline, arsenic trioxide, hydroxyurea, and pharmaceutically acceptable salts thereof.

In another aspect, the present invention provides a combination comprising the compound of formula (I), or a pharmaceutically acceptable salt thereof, and one or more therapeutic agents selected from a retinoic acid analogue, a nucleoside analogue, a DOT1L inhibitor, a HDAC inhibitor, a demethylating agent, an FLT3 inhibitor, a BCL2 inhibitor, an MDM2 inhibitor, a c-KIT inhibitor, a BET inhibitor, an anthracycline, arsenic trioxide, hydroxyurea, and pharmaceutically acceptable salts thereof, for use as a therapeutically active substance.

In another aspect, the present invention is directed to a combination comprising the compound of formula (I), or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof, for use in the treatment of an hematological malignancy. In certain embodiments, said hematological malignancy is a myeloid hematological malignancy. In certain embodiments, said hematological malignancy is a lymphoid hematological malignancy.

In another aspect, the present invention is directed to a method for treating a hematological malignancy in a patient in need thereof, comprising administering a therapeutically effective amount of compound of formula (I), or a pharmaceutically acceptable salt thereof, and a therapeutically effective amount of one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof. In certain embodiments, said hematological malignancy is a myeloid hematological malignancy. In certain embodiments, said hematological malignancy is a lymphoid hematological malignancy.

In another aspect, the present invention is directed to a method for treating a hematological malignancy in a patient in need thereof, comprising administering to said patient a therapeutically effective amount of combination comprising the compound of formula (I), or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof. In certain embodiments, said hematological malignancy is a myeloid hematological malignancy. In certain embodiments, said hematological malignancy is a lymphoid hematological malignancy.

In another aspect, the present invention provides the use of a combination comprising the compound of formula (I), or a pharmaceutically acceptable salt thereof, and one or more therapeutic agents selected from a retinoic acid analogue, a nucleoside analogue, a DOT1L inhibitor, a HDAC inhibitor, a demethylating agent, an FLT3 inhibitor, a BCL2 inhibitor, an MDM2 inhibitor, a c-KIT inhibitor, a BET inhibitor, an anthracycline, arsenic trioxide, hydroxyurea, and pharmaceutically acceptable salts thereof, for the treatment of hematological malignancies. In certain embodiments, said hematological malignancy is a myeloid hematological malignancy. In certain embodiments, said hematological malignancy is a lymphoid hematological malignancy.

In a further aspect, the present invention provides the use of a combination comprising the compound of formula (I), or a pharmaceutically acceptable salt thereof, and one or more therapeutic agents selected from a retinoic acid analogue, a nucleoside analogue, a DOT1L inhibitor, a HDAC inhibitor, a demethylating agent, an FLT3 inhibitor, a BCL2 inhibitor, an MDM2 inhibitor, a c-KIT inhibitor, a BET inhibitor, an anthracycline, arsenic trioxide, hydroxyurea, and pharmaceutically acceptable salts thereof, for the preparation of a medicament for the treatment of hematological malignancies. In certain embodiments, said hematological malignancy is a myeloid hematological malignancy. In certain embodiments, said hematological malignancy is a lymphoid hematological malignancy.

In another aspect, the present invention is directed to a method for treating a hematological malignancy in a patient in need thereof, comprising administering to said patient a pharmaceutical composition comprising the compound of formula (I), or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof, and one or more pharmaceutically acceptable excipients. In certain embodiments, said hematological malignancy is a myeloid hematological malignancy. In certain embodiments, said hematological malignancy is a lymphoid hematological malignancy.

In a further aspect, the present invention provides a pharmaceutical composition comprising the compound of formula (I), or a pharmaceutically acceptable salt thereof, and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof, and one or more pharmaceutically acceptable excipients.

ORY-1001:

The compound of formula (I)

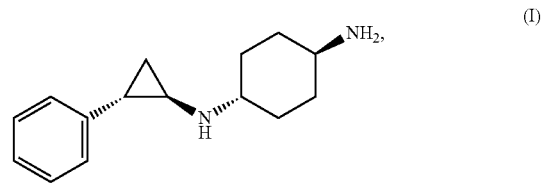 [SMILES: N[C@H]1CC[C@H](N[C@@H]2C[C@H]2c2ccccc2)CC1]

[CAS Reg. No. 1431304-21-0], also known as ORY-1001 or (trans)-N1-((1R,2S)-2-phenylcyclopropyl)cyclohexane-1,4-diamine, has been described e.g. in Example 5 of International Patent Application WO 2013/057322[2]. Pharmaceutically acceptable salts thereof are also described therein, including hydrochloride salts [CAS Reg. No. 1431303-72-8, dihydrochloride]. Most particular pharmaceutically acceptable salt is a dihydrochloride salt. The compound of formula (I) acts as a selective LSD1 inhibitor.

Retinoic Acid Analogues:

Tretinoin [CAS Reg. No. 302-79-4], also known and referred to as ATRA or all-trans retinoic acid, has been described e.g. in U.S. Pat. No. 2,709,712[3] or in the Recommended INN List 11[4]. Tretinoin causes the immature promyelocytes to differentiate. ATRA is one of the current standards of care for treatment of acute leukemia.

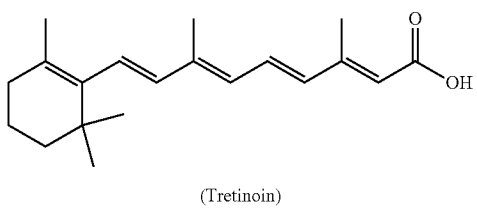 [SMILES: CC1=C(/C=C/C(C)=C/C=C/C(C)=C/C(=O)O)C(C)(C)CCC1]

(Tretinoin)

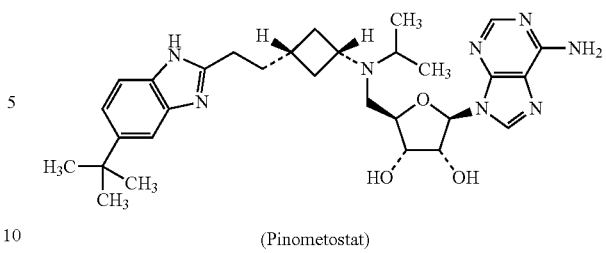

(Pinometostat)

ATRA derivatives reported in the literature with anticancer, particularly antileukemia activity, can also be used in the combinations of the invention.

Nucleoside Analogues:

Nucleoside analogues are nucleosides which contain a nucleic acid analogue and a sugar and are used as therapeutic drugs against a range of disorders, including some being used in chemotherapy. A preferred nucleoside analogue for use in the combinations of the invention is Cytarabine.

Cytarabine [CAS Reg. No. 147-94-4], also known and referred to as ARA-C or arabinofuranosyl cytidine, has been described e.g. in Chu M. Y. et al.[5] or in the Recommended INN List 6[6]. Cytarabine converts rapidly into cytosine arabinoside triphosphate, which damages DNA when the cell cycle holds in the S phase during DNA synthesis. ARA-C is one of the current standards of care for treatment of acute leukemia, usually in combination with an anthracycline such as daunorubicin

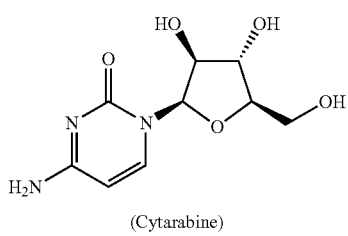 [SMILES: Nc1ccn([C@@H]2O[C@H](CO)[C@@H](O)[C@@H]2O)c(=O)n1]

(Cytarabine)

Other nucleoside analogues that can be used in the combinations of the invention include, but are not limited to sapacitabine, clofarabine, elacytarabine, fludarabine, cytarabine octosfate, gemcitabine, 2-chloro-2-deoxyadenosine (also known as 2-CDA), troxacitabine, forodesine and nelarabine.

DOT1L Inhibitors:

DOT1L is a histone methyltransferase that has been reported to be involved in leukemia, particularly in certain subtypes of AML and ALL, and inhibitors of DOT1L are under development for the treatment of leukemia. Any known DOT1L inhibitor can in principle be used in the combinations of the invention. Examples of DOT1L inhibitors that can be used include without limitation pinometostat, EPZ-004777, and SGC-0946. A preferred DOT1L inhibitor for use in the combinations of the invention is Pinometostat.

Pinometostat [CAS Reg. No. 1380288-87-8], also known and referred to as EPZ-5676, has been described e.g. in International Patent Application WO 2012075381[7] or in the Proposed INN List 112[8]. Pinometostat acts as DOT1L inhibitor.

EPZ-004777 [CAS Reg. No. 1338466-77-5], also known as 7-[5-Deoxy-5-[[3-[[[[4-(1,1-dimethylethyl)phenyl]amino]carbonyl]amino]propyl](1-methylethyl)amino]-β-D-ribofuranosyl]-7H-pyrrolo[2,3-d]pyrimidin-4-amine, has been described e.g. in Daigle S. R. et al.[9]. EPZ-004777 acts as DOT1L inhibitor.

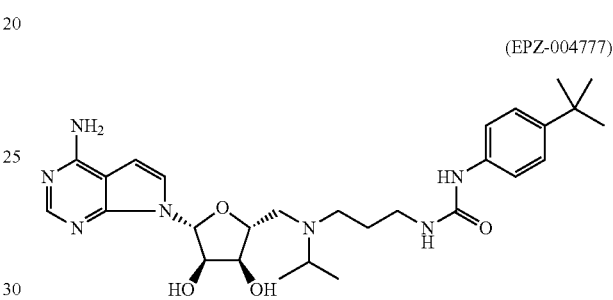

(EPZ-004777)

SGC0496 (CAS Reg No. 1561178-17-3) is the compound 1-[3-[[[(2R,3S,4R,5R)-5-(4-Amino-5-bromo-7H-pyrrolo[2,3-d]pyrimidin-7-yl)-3,4-dihydroxytetrahydrofuran-2-yl]methyl](isopropyl)amino]propyl]-3-[4-(2,2-dimethylethyl)phenyl]urea, and has been described in Yu et al.[10]. SGC0496 has the following chemical structure:

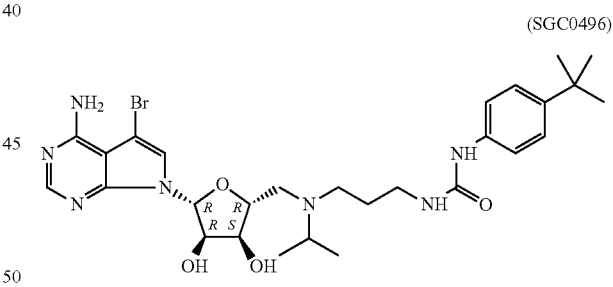

(SGC0496)

HDAC Inhibitors

Histone deactetylase (HDAC) inhibitors are a class of compounds that interfere with the function of histone deacetylase which are approved or under clinical development for the treatment of several times of cancers. Any known HDAC inhibitor can in principle be used in the combinations of the invention. Preferred HDAC inhibitors for use in the combinations of the invention are Belinostat, Panobinostat, Vorinostat, Ricolinostat, Entinostat, Mocetinostat, Abexinostat, Resminostat, Givinostat or Quisinostat.

Vorinostat [CAS Reg. No. 149647-78-9], also known and referred to as SAHA or suberanilohydroxamic acid, has been described e.g. in International Patent Application WO 9307148[11] or in the Recommended INN List 56[12]. Vorinostat acts as histone deacetylase (HDAC) inhibitor.

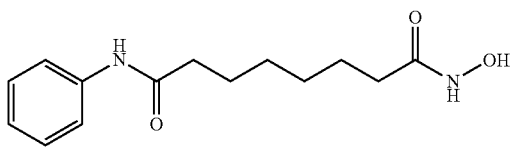

(Vorinostat)

Ricolinostat [CAS Reg. No. 1316214-52-4], also known and referred to as Rocilinostat and ACY-1215, has been described e.g. in International Patent Application WO 2011091213[13] or in the Recommended INN List 71[14]. Ricolinostat acts as histone deacetylase (HDAC) inhibitor.

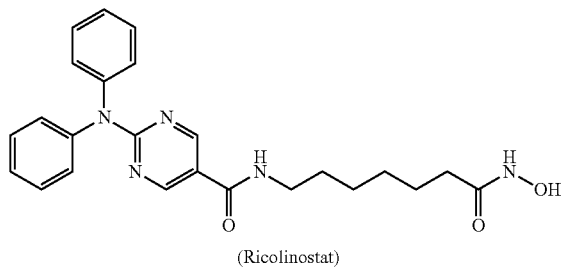 [SMILES: O=C(CCCCCCNC(=O)c1cnc(N(c2ccccc2)c2ccccc2)nc1)NO]

(Ricolinostat)

Entinostat [CAS Reg. No. 209783-80-2], also known as SNDX-275, has been described e.g. in Japanese Patent Application JP 10152462[15] or in the Recommended INN List 61[16]. Entinostat acts as histone deacetylase (HDAC) inhibitor.

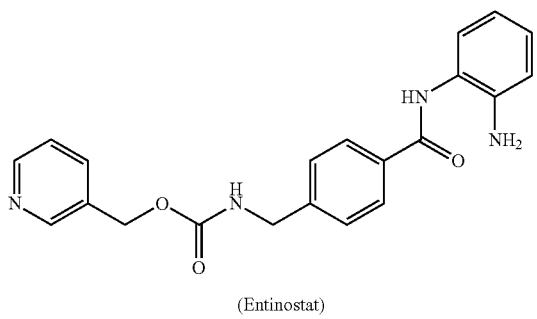 [SMILES: Nc1ccccc1NC(=O)c1ccc(CNC(=O)OCc2cccnc2)cc1]

(Entinostat)

Belinostat (CAS Reg No 866323-14-0), also known as (22E)-N-Hydroxy-3-[3-(phenylsulfamoyl)phenyl]prop-2-enamide, has been disclosed in WO 2009/040517[17]. The compound has the following chemical structure:

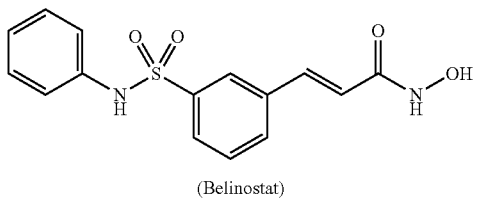 [SMILES: O=C(/C=C/c1cccc(S(=O)(=O)Nc2ccccc2)c1)NO]

(Belinostat)

Panobinostat (CAS Reg No 404950-80-7), also known as (2E)-N-hydroxy-3-[4-({[2-(2-methyl-1H-indol-3-yl)ethyl]amino}methyl)phenyl]acrylamide, has been disclosed in WO 02/022577[18]. The compound has the following chemical structure:

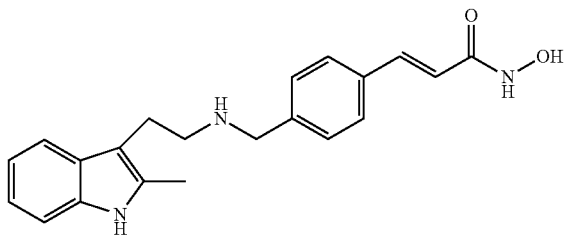

(Panobinostat)

Demethylating Agents

Also known as hypomethylating agents, these are drugs that inhibit DNA methylation, particularly by blocking the activity of DNA methyltransferase (DNMT inhibitors). Currently two members of this class (decitabine and azacitidine) are FDA-approved for the treatment of myelodysplastic syndrome and are being investigated for use in a number of tumors, including AML[19]. DNMT inhibitors that can be used according to the invention include but are not limited to:

Decitabine [CAS Reg. No. 2353-33-5], also known as 5-aza-2'-deoxycytidine, has been described e.g. in Wolfrom I. M. L. et al.[20] or in the Recommended INN List 30[21].

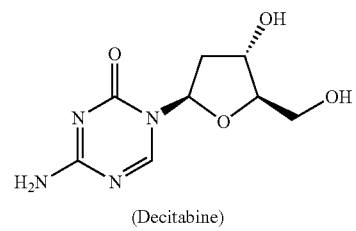 [SMILES: Nc1ncn([C@H]2C[C@H](O)[C@@H](CO)O2)c(=O)n1]

(Decitabine)

Azacitidine [CAS Reg. No. 320-67-2] has been described e.g. in German Patent DE 1140941[22] or in the Recommended INN List 19[23]. Azacitidine is one of the current standards of care for treatment of acute leukemia.

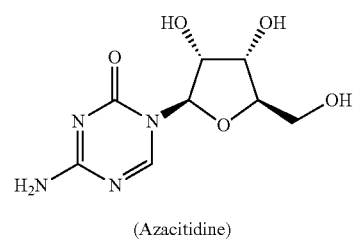 [SMILES: Nc1ncn([C@@H]2O[C@H](CO)[C@@H](O)[C@H]2O)c(=O)n1]

(Azacitidine)

Guadecitabine, also known as SGI-110. This compound is a decitabine linked via phosphodiester bond to a guanosine and acts as a prodrug of decitabine. Following metabolic activation by phosphorylation and incorporation into DNA, guadecitabine inhibits DNA methyltransferase, thereby causing genome-wide and non-specific hypomethylation and inducing cell cycle arrest at S-phase. This agent is resistant to cytidine deaminase, hence may result in gradual release of decitabine both extra- and intracellularly, leading to more prolonged exposures to decitabine.

Zebularine, 5-fluoro-2'-deoxycytidine, 2'-deoxy-5,6-dihydro-5,6-azacytidine, hydralazine, procainamide, hydralazine, EGCG and RG108 are other DNMT inhibitors that can be used in the combinations of the invention.

FLT3 Inhibitors:

FMS-related tyrosine kinase 3 (FLT3) is a proto-oncogene. Mutations of the FTL3 receptor can lead to the development of leukemia, and indeed is one of the most frequently mutated genes in AML. FLT3 inhibitors are being developed for the treatment of several types of cancers. Any known FLT3 inhibitor can in principle be used in the combinations of the invention. Preferred FLT3 inhibitors for use in the combinations of the invention include Quizartinib, Sorafenib, Sunitinib and Lestaurtinib.

Quizartinib [CAS Reg. No. 950769-58-1] has been described e.g. in International Patent Application WO 2007109120[24] or in the Recommended INN List 99[25].

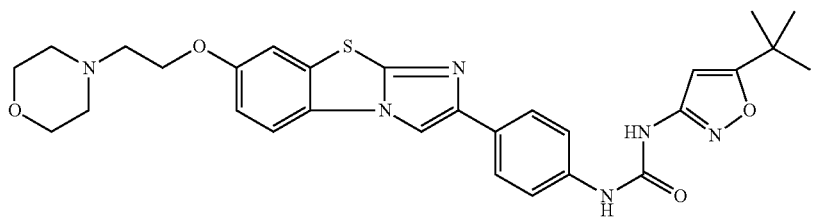

(Quizartinib)

BCL2 Inhibitors:

Bcl2 (B cell lymphoma 2) is considered an important antiapoptotic protein and is classified as an oncogene. Alterations in the BCL2 gene have been identified as a cause of a number of cancers and Bcl2 inhibitors are being developed as anticancer therapy. Any known Bcl2 inhibitor can be used in the combinations of the invention. Preferred Bcl2 inhibitors include ABT-737, Navitoclax (aka ABT-263), Venetoclax (aka ABT-199), and Obatoclax ABT-737 [CAS Reg. No. 852808-04-9], also known as 4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide, has been described e.g. in International Patent Application WO 2005049594[26].

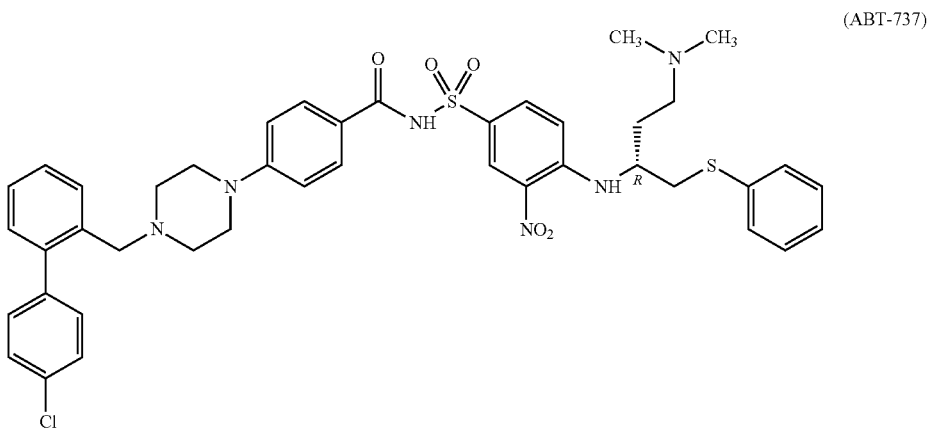

(ABT-737)

Navitoclax [CAS Reg. No. 923564-51-6], also known as ABT-263 or 4-(4-{[2-(4-Chlorophenyl)-5,5-dimethyl-1-cyclohexen-1-yl]methyl}-1-piperazinyl)-N-[(4-{[(2R)-4-(4-morpholinyl)-1-(phenylsulfanyl)-2-butanyl]amino}-3-[(trifluoromethyl) sulfonyl]phenyl)-sulfonyl]benzamide, has been described e.g. in US 20070027135[27].

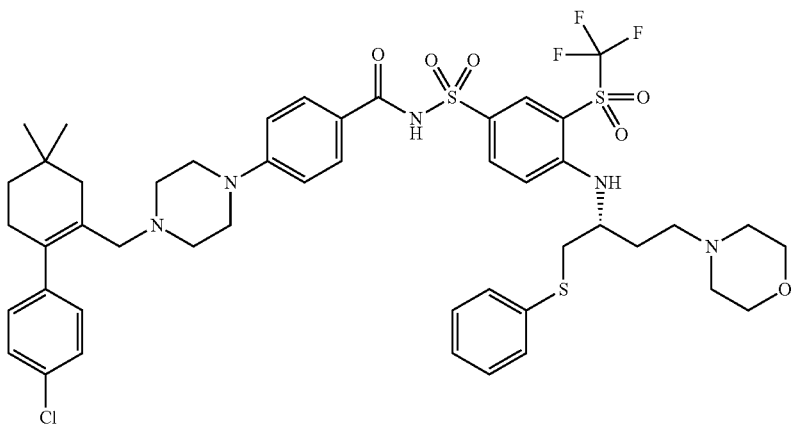

(ABT-263 (Navitoclax))

Obatoclax [CAS Reg. No. 803712-67-6], also known as 2-(2-((3,5-Dimethyl-1H-pyrrol-2-yl)methylene)-3-methoxy-2H-pyrrol-5-yl)-1H-indole, has been described e.g. in International Patent Application WO 2004106328[28].

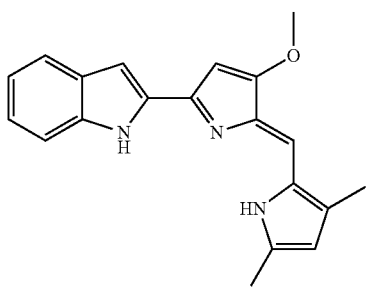

(Obatoclax)

Venetoclax [CAS Reg. No. 1257044-40-8], also known as ABT-199 or 4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide, has been described e.g. in International Patent Application WO 2010138588[29].

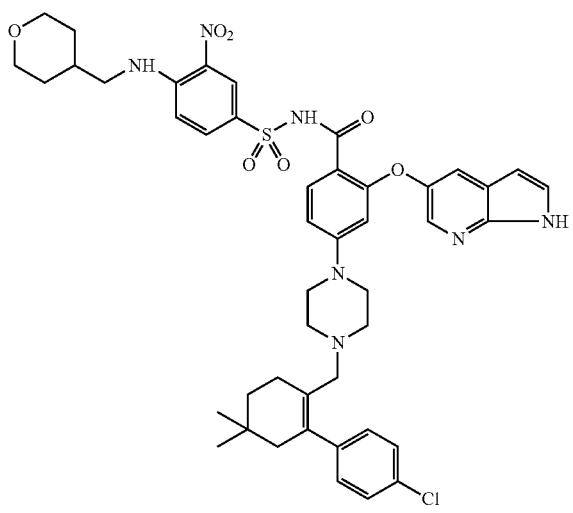

(ABT-199 (Venetoclax))

MDM2 Inhibitors:

Mouse double minute 2 homolog (MDM2) is considered an important negative regulator of the p53 tumor suppressor, among other roles in cancer. Mdm2 inhibitors are compounds which inhibit the interaction between Mdm2 and p53 and include Nutlins, among others. A particularly preferred Mdm2 inhibitor is Nutlin-3A.

Nutlin-3A [CAS Reg. No. 675576-98-4], also known as 4-[[(4S,5R)-4,5-bis(4-chlorophenyl)-4,5-dihydro-2-[4-methoxy-2-(1-methylethoxy)phenyl]-1H-imidazol-1-yl]carbonyl]-2-piperazinone, has been described e.g. in US Patent Application US 20050282803[30].

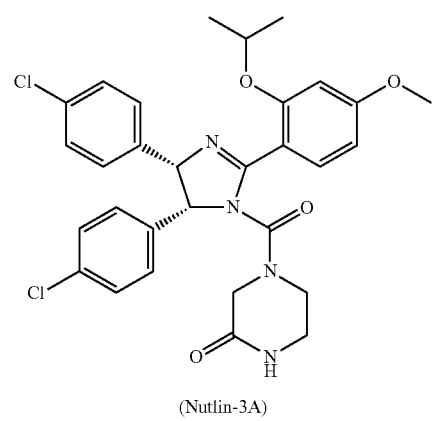 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(Nutlin-3A)

c-KIT Inhibitors:

c-KIT (also known as Mast/stem cell growth factor receptor (SCGFR) or CD117) is a receptor tyrosine kinase protein that in humans is a proto-oncogene. Activating mutations in this gene are associated with a number of cancers, including acute myeloid leukemia. Any disclosed cKIT inhibitor can be used in the combinations of the invention. A suitable c-KIT inhibitor is dasatinib or imatinib.

Dasatinib (CAS Reg No 302962-49-8), is the compound N-(2-chloro-6-methylphenyl)-2-[[6-[4-(2-hydroxyethyl)-1-piperazinyl]-2-methyl-4-pyrimidinyl]amino]-5-thiazolecarboxamide, with formula:

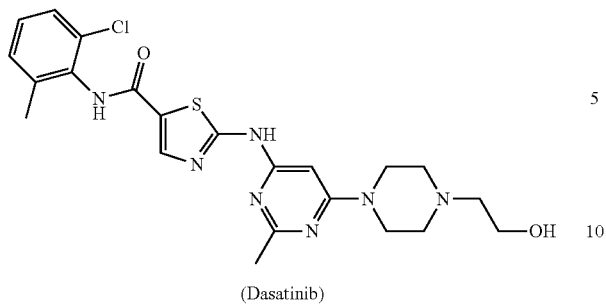

(Dasatinib)

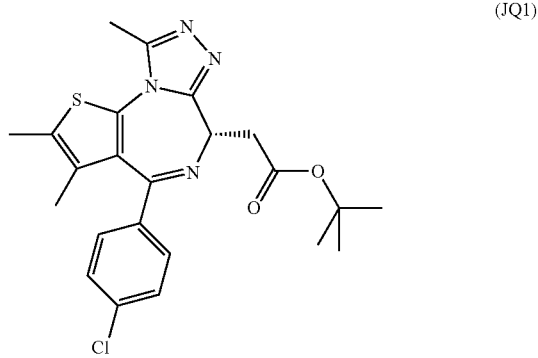 [SMILES: Cc1sc2c(c1C)C(c1ccc(Cl)cc1)=N[C@@H](CC(=O)OC(C)(C)C)c1nnc(C)n1-2]

(JQ1)

Dasatinib is approved for first line use in patients with chronic myelogenous leukemia (CML) and acute lymphoblastic leukemia (ALL).

Imatinib (CAS Reg No 152459-95-5), is the compound 4-[(4-methylpiperazin-1-yl)methyl]-N-(4-methyl-3-{[4-(pyridin-3-yl)pyrimidin-2-yl]amino}phenyl)benzamide, with formula:

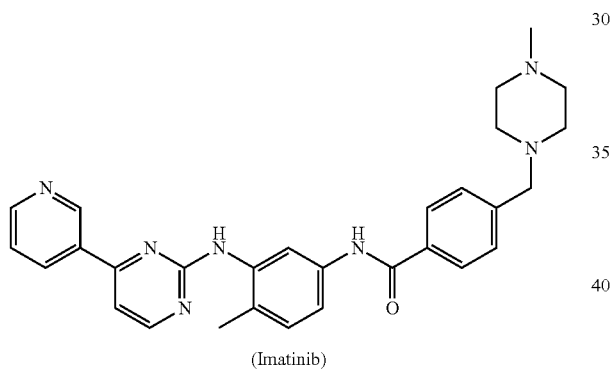

(Imatinib)

Imatinib is a tyrosine kinase inhibitor used in the treatment of multiple cancers, including Philadelphia-chromosome positive CML.

Bet Inhibitors:

BET inhibitors are a class of drugs with anti-cancer, immunosuppressive, and other effects currently in clinical trials. These molecules reversibly bind the bromodomains of Bromodomain and Extra-Terminal motif (BET) proteins BRD2, BRD3, BRD4, and BRDT, and prevent protein-protein interaction between BET proteins and acetylated histones and transcription factors. Any reported BET inhibitor can be used in the combinations of the invention. Examples of BET inhibitors include without limitation:

JQ1 (CAS Reg No 1268524-70-4) is (S)-tert-butyl 2-(4-(4-chlorophenyl)-2,3,9-trimethyl-6H-thieno[3,2-f][1,2,4]triazolo[4,3-a][1,4]diazepin-6-yl)acetate and is disclosed in WO 2011143651[31].

GSK1210151A (I-BET 151) (CAS Reg No 1300031-49-5) is 7,3,5-dimethyl-4-isoxazolyl-1,3-dihydro-8-methoxy-1-[1R-1-(2-pyridinyl)ethyl]-2H-imidazo[4,5-c]quinolin-2-one and is disclosed in WO 2011054843[32].

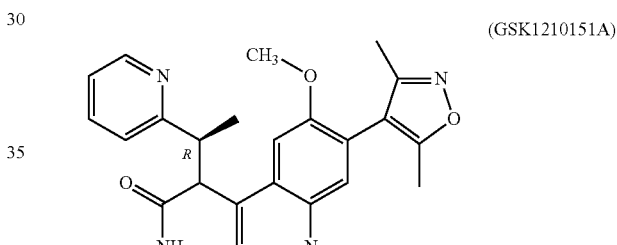

(GSK1210151A)

MS 436 (CAS Reg No 1395084-25-9) is 4-[(1E)-2-(2-amino-4-hydroxy-5-methylphenyl)diazenyl]-N-2-pyridinyl-benzenesulfonamide and is disclosed in WO 2012116170[33].

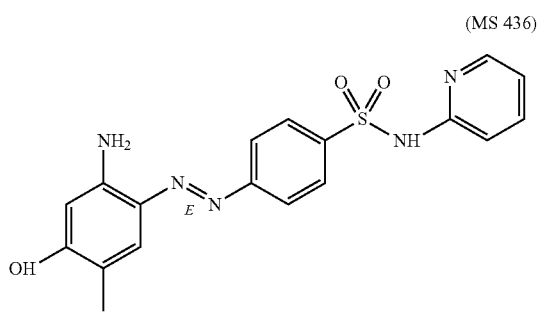 [SMILES: Cc1cc(/N=N/c2ccc(S(=O)(=O)Nc3ccccn3)cc2)c(N)cc1O]

(MS 436)

I-BET 762 (GSK525762) is:

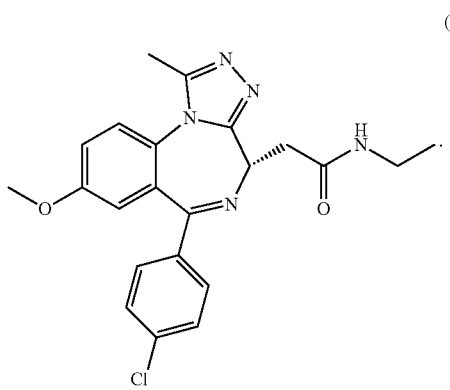

(I-BET 762)

OTX-015 (CAS Reg No 202590-98-5) is (6S)-4-(4-chlorophenyl)-N-(4-hydroxyphenyl)-2,3,9-trimethyl-6H-Thieno[3,2-f][1,2,4]triazolo[4,3-a][1,4]diazepine-6-acetamide and is disclosed in U.S. Pat. No. 5,712,274[34].

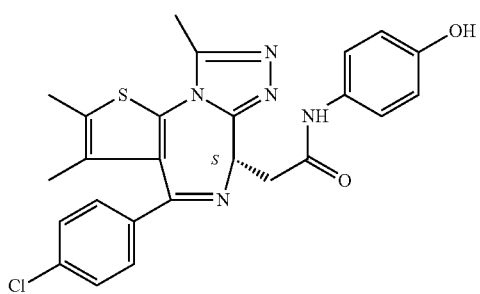

(OTX-015)

CPI-203 (CAS Reg No 1446144-04-2) is (6S)-4-(4-chlorophenyl)-2,3,9-trimethyl-6H-thieno[3,2-f][1,2,4]triazolo[4,3-a][1,4]diazepine-6-acetamide and has been disclosed in WO 2014134583[35].

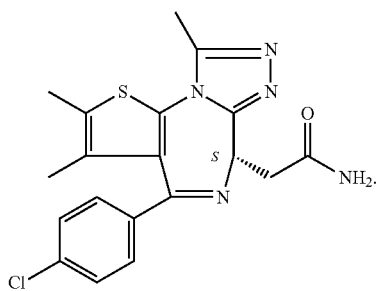

(CPI203)

GSK1324726A (I-BET726) (CAS Reg No 1300031-52-0) is 4-[(2S,4R)-1-acetyl-4-[(4-chlorophenyl)amino]-1,2,3,4-tetrahydro-2-methyl-6-quinolinyl]-benzoic acid and has been disclosed in WO 2011054843[36].

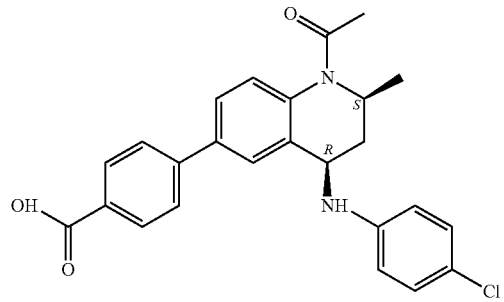

(GSK1324726)

Other BET inhibitors that can be used in combination with a compound of formula (I) include ABBV-075, BAY1238097, CPI-0610 and TEN-010.

Anthracyclines:

Anthracyclines (or anthracycline antibiotics) are a class of drugs used in cancer chemotherapy derived from *Streptomyces* bacterium *Streptomyces peucetius* var. *caesius*. These compounds are used to treat many cancers, including leukemias. Examples of anthracyclines for use in the combinations of the invention include doxorubicin, idarubicin, and daunorubicin.

Anthracyclines such as daunorubicin, doxorubicin an idarubicin are commonly used to treat specific types of leukemia (e.g. acute myeloid leukemia and acute lymphocytic leukemia), usually in combination with other chemotherapy drugs such as cytarabine.

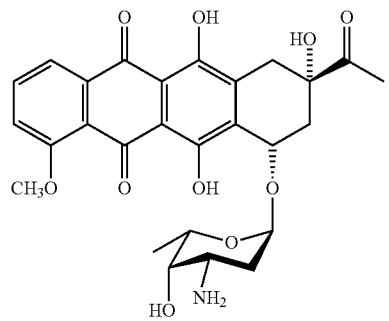

(Daunorubicin)

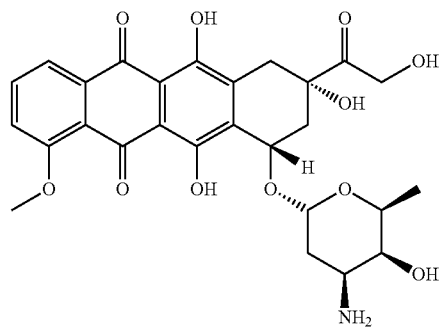

(Doxorubicin)

-continued

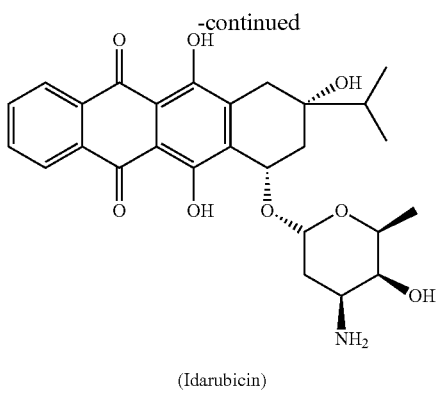

(Idarubicin)

Arsenic Trioxide:

Arsenic trioxide is a chemotherapeutic agent approved by the US FDA for the treatment of acute promyelocytic leukemia that is unresponsive to "first line" agents, such as ATRA. It has been shown that arsenic trioxide induces cancer cells to undergo apoptosis. Use as a cytostatic in the treatment of refractory promyelocytic (M3) subtype of acute myeloid leukemia. The combination therapy of arsenic trioxide and all-trans retinoic acid (ATRA) has been approved by the FDA for treatment of certain leukemias. A liquid form of arsenic trioxide that can be administered orally has been developed.

Hydroxyurea:

Hydroxyurea (CAS Reg No. 127-07-1), also known as Hydroxycarbamide, is an antineoplastic drug used in myeloproliferative disorders, including CML. Hydroxycarbamide decreases the production of deoxyribonucleotides via inhibition of the enzyme ribonucleotide reductase by scavenging tyrosyl free radicals as they are involved in the reduction NDPs.

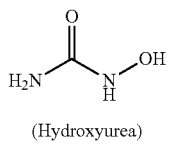

(Hydroxyurea)

ATRA, ARA-C (optionally in combination with an anthracycline such as daunorubicin or idarubicin) and Azacitidine are the current standards of care for treatment of acute leukemia.

In certain embodiments, the retinoic acid analogue is tretinoin.

In certain embodiments, the nucleoside analogue is cytarabine.

In certain embodiments, the DOT1L inhibitor is selected from pinometostat and EPZ-004777.

In certain embodiments, the HDAC inhibitor is selected from vorinostat, ricolinostat, and entinostat.

In certain embodiments, the DNMT inhibitor is selected from decitabine, and azacitidine.

In certain embodiments, the FLT3 inhibitor is quizartinib.

In certain embodiments, the BCL2 inhibitor is ABT-737.

In certain embodiments, the MDM2 inhibitor is Nutlin-3A.

In certain embodiments, the c-KIT inhibitor is dasatinib.

In certain embodiments, the BET inhibitor is JQ-1.

In certain embodiments, the anthracycline is daunorubicin.

Another embodiment relates to a combination comprising the compound of formula (I) or a pharmaceutically acceptable salt thereof, and one or more therapeutic agents selected from tretinoin, cytarabine, sapacitabine, clofarabine, elacytarabine, fludarabine, cytarabine ocfosfate, gemcitabine, 2-chloro-2-deoxyadenosine (also known as 2-CDA), troxacitabine, forodesine, nelarabine, pinometostat, EPZ-004777, SGC-0946, Belinostat, Panobinostat, Vorinostat, Ricolinostat, Entinostat, Mocetinostat, Abexinostat, Resminostat, Givinostat, Quisinostat, decitabine, azacitidine, guadecitabine, Quizartinib, Sorafenib, Sunitinib, Lestaurtinib, ABT-737, Navitoclax, Venetoclax, Obatoclax, Nutlin-3A, dasatinib, imatinib, JQ1, GSK1210151A, MS 436, GSK525762, OTX-015, CPI-203, GSK1324726A, daunorubicin, doxorubicin, idarubicin, arsenic trioxide, hydroxyurea, and pharmaceutically acceptable salts thereof. In a particular embodiment, the combination comprises the compound of formula (I) or a pharmaceutically acceptable salt thereof, and one or more therapeutic agents selected from tretinoin, cytarabine, pinometostat, EPZ-00477, Vorinostat, Ricolinostat, Entinostat, decitabine, azacitidine, Quizartinib, ABT-737, Nutlin-3A, dasatinib, JQ1, daunorubicin, arsenic trioxide, hydroxyurea, and pharmaceutically acceptable salts thereof.

Another embodiment relates to a pharmaceutical composition comprising the compound of formula (I) or a pharmaceutically acceptable salt thereof, and one or more therapeutic agents selected from tretinoin, cytarabine, sapacitabine, clofarabine, elacytarabine, fludarabine, cytarabine ocfosfate, gemcitabine, 2-chloro-2-deoxyadenosine (also known as 2-CDA), troxacitabine, forodesine, nelarabine, pinometostat, EPZ-004777, SGC-0946, Belinostat, Panobinostat, Vorinostat, Ricolinostat, Entinostat, Mocetinostat, Abexinostat, Resminostat, Givinostat, Quisinostat, decitabine, azacitidine, guadecitabine, Quizartinib, Sorafenib, Sunitinib, Lestaurtinib, ABT-737, Navitoclax, Venetoclax, Obatoclax, Nutlin-3A, dasatinib, imatinib, JQ1, GSK1210151A, MS 436, GSK525762, OTX-015, CPI-203, GSK1324726A, daunorubicin, doxorubicin, idarubicin, arsenic trioxide, hydroxyurea, and pharmaceutically acceptable salts thereof, and one or more pharmaceutically acceptable excipient. In a particular embodiment, the pharmaceutical composition comprises the compound of formula (I) or a pharmaceutically acceptable salt thereof, and one or more therapeutic agents selected from tretinoin, cytarabine, pinometostat, EPZ-00477, Vorinostat, Ricolinostat, Entinostat, decitabine, azacitidine, Quizartinib, ABT-737, Nutlin-3A, dasatinib, JQ1, daunorubicin, arsenic trioxide, hydroxyurea, and pharmaceutically acceptable salts thereof, and one or more pharmaceutically acceptable excipient.

Another embodiment relates to a combination comprising the compound of formula (I) or a pharmaceutically acceptable salt thereof, and one or more therapeutic agents selected from tretinoin, cytarabine, sapacitabine, clofarabine, elacytarabine, fludarabine, cytarabine ocfosfate, gemcitabine, 2-chloro-2-deoxyadenosine (also known as 2-CDA), troxacitabine, forodesine, nelarabine, pinometostat, EPZ-004777, SGC-0946, Belinostat, Panobinostat, Vorinostat, Ricolinostat, Entinostat, Mocetinostat, Abexinostat, Resminostat, Givinostat, Quisinostat, decitabine, azacitidine, guadecitabine, Quizartinib, Sorafenib, Sunitinib, Lestaurtinib, ABT-737, Navitoclax, Venetoclax, Obatoclax, Nutlin-3A, dasatinib, imatinib, JQ1, GSK1210151A, MS 436, GSK525762, OTX-015, CPI-203, GSK1324726A, daunorubicin, doxorubicin, idarubicin, arsenic trioxide, hydroxyurea, and pharmaceutically acceptable salts thereof, for use as therapeutically active substance. In a particular embodiment, the combination comprises the compound of formula (I) or a pharmaceutically acceptable salt thereof, and one or more therapeutic agents selected from tretinoin, cytarabine, pinometostat, EPZ-00477, Vorinostat, Ricolinostat, Entinostat, decitabine, azacitidine, Quizartinib, ABT-737, Nutlin-3A, dasatinib, JQ1, daunorubicin, arsenic trioxide, hydroxyurea, and pharmaceutically acceptable salts thereof, for use as a therapeutically active substance.

Another embodiment relates to a combination comprising the compound of formula (I) or a pharmaceutically acceptable salt thereof, and one or more therapeutic agents selected from tretinoin, cytarabine, sapacitabine, clofarabine, elacytarabine, fludarabine, cytarabine ocfosfate, gemcitabine, 2-chloro-2-deoxyadenosine (also known as 2-CDA), troxacitabine, forodesine, nelarabine, pinometostat, EPZ-004777, SGC-0946, Belinostat, Panobinostat, Vorinostat, Ricolinostat, Entinostat, Mocetinostat, Abexinostat, Resminostat, Givinostat, Quisinostat, decitabine, azacitidine, guadecitabine, Quizartinib, Sorafenib, Sunitinib, Lestaurtinib, ABT-737, Navitoclax, Venetoclax, Obatoclax, Nutlin-3A, dasatinib, imatinib, JQ1, GSK1210151A, MS 436, GSK525762, OTX-015, CPI-203, GSK1324726A, daunorubicin, doxorubicin, idarubicin, arsenic trioxide, hydroxyurea, and pharmaceutically acceptable salts thereof, for use in the treatment of a hyperproliferative disorder. In a particular embodiment, the combination comprises the compound of formula (I) or a pharmaceutically acceptable salt thereof, and one or more therapeutic agents selected from tretinoin, cytarabine, pinometostat, EPZ-00477, Vorinostat, Ricolinostat, Entinostat, decitabine, azacitidine, Quizartinib, ABT-737, Nutlin-3A, dasatinib, JQ1, daunorubicin, arsenic trioxide, hydroxyurea, and pharmaceutically acceptable salts thereof, for use in the treatment of a hematological malignancy. In certain embodiments, said hematological malignancy is a myeloid hematological malignancy. In certain embodiments, said hematological malignancy is a lymphoid hematological malignancy.

Another embodiment relates to a method for the treatment of a hematological malignancy in a patient in need thereof, which method comprises administering a therapeutically effective amount of combination comprising the compound of formula (I) or a pharmaceutically acceptable salt thereof, and one or more therapeutic agents selected from tretinoin, cytarabine, sapacitabine, clofarabine, elacytarabine, fludarabine, cytarabine ocfosfate, gemcitabine, 2-chloro-2-deoxyadenosine (also known as 2-CDA), troxacitabine, forodesine, nelarabine, pinometostat, EPZ-004777, SGC-0946, Belinostat, Panobinostat, Vorinostat, Ricolinostat, Entinostat, Mocetinostat, Abexinostat, Resminostat, Givinostat, Quisinostat, decitabine, azacitidine, guadecitabine, Quizartinib, Sorafenib, Sunitinib, Lestaurtinib, ABT-737, Navitoclax, Venetoclax, Obatoclax, Nutlin-3A, dasatinib, imatinib, JQ1, GSK1210151A, MS 436, GSK525762, OTX-015, CPI-203, GSK1324726A, daunorubicin, doxorubicin, idarubicin, arsenic trioxide, hydroxyurea, and pharmaceutically acceptable salts thereof to said patient. In a particular embodiment, the method comprises administering a therapeutically effective amount of combination comprising the compound of formula (I) or a pharmaceutically acceptable salt thereof, and one or more therapeutic agents selected from tretinoin, cytarabine, pinometostat, EPZ-00477, Vorinostat, Ricolinostat, Entinostat, decitabine, azacitidine, Quizartinib, ABT-737, Nutlin-3A, dasatinib, JQ1, daunorubicin, arsenic trioxide, hydroxyurea, and pharmaceutically acceptable salts thereof. In certain embodiments, said hematological malignancy is a myeloid hematological malignancy. In certain embodiments, said hematological malignancy is a lymphoid hematological malignancy.

Another embodiment relates to the use of a combination comprising the compound of formula (I) or a pharmaceutically acceptable salt thereof, and one or more therapeutic agents selected from tretinoin, cytarabine, sapacitabine, clofarabine, elacytarabine, fludarabine, cytarabine ocfosfate, gemcitabine, 2-chloro-2-deoxyadenosine (also known as 2-CDA), troxacitabine, forodesine, nelarabine, pinometostat, EPZ-004777, SGC-0946, Belinostat, Panobinostat, Vorinostat, Ricolinostat, Entinostat, Mocetinostat, Abexinostat, Resminostat, Givinostat, Quisinostat, decitabine, azacitidine, guadecitabine, Quizartinib, Sorafenib, Sunitinib, Lestaurtinib, ABT-737, Navitoclax, Venetoclax, Obatoclax, Nutlin-3A, dasatinib, imatinib, JQ1, GSK1210151A, MS 436, GSK525762, OTX-015, CPI-203, GSK1324726A, daunorubicin, doxorubicin, idarubicin, arsenic trioxide, hydroxyurea, and pharmaceutically acceptable salts thereof for the treatment of a hematological malignancy. In a particular embodiment, the combination comprises the compound of formula (I) or a pharmaceutically acceptable salt thereof, and one or more therapeutic agents selected from tretinoin, cytarabine, pinometostat, EPZ-00477, Vorinostat, Ricolinostat, Entinostat, decitabine, azacitidine, Quizartinib, ABT-737, Nutlin-3A, dasatinib, JQ1, daunorubicin, arsenic trioxide, hydroxyurea, and pharmaceutically acceptable salts thereof for the treatment of a hematological malignancy. In certain embodiments, said hematological malignancy is a myeloid hematological malignancy. In certain embodiments, said hematological malignancy is a lymphoid hematological malignancy.

Another embodiment relates to the use of a combination comprising the compound of formula (I) or a pharmaceutically acceptable salt thereof, and one or more therapeutic agents selected from tretinoin, cytarabine, sapacitabine, clofarabine, elacytarabine, fludarabine, cytarabine ocfosfate, gemcitabine, 2-chloro-2-deoxyadenosine (also known as 2-CDA), troxacitabine, forodesine, nelarabine, pinometostat, EPZ-004777, SGC-0946, Belinostat, Panobinostat, Vorinostat, Ricolinostat, Entinostat, Mocetinostat, Abexinostat, Resminostat, Givinostat, Quisinostat, decitabine, azacitidine, guadecitabine, Quizartinib, Sorafenib, Sunitinib, Lestaurtinib, ABT-737, Navitoclax, Venetoclax, Obatoclax, Nutlin-3A, dasatinib, imatinib, JQ1, GSK1210151A, MS 436, GSK525762, OTX-015, CPI-203, GSK1324726A, daunorubicin, doxorubicin, idarubicin, arsenic trioxide, hydroxyurea, and pharmaceutically acceptable salts thereof for the preparation of medicaments useful in the treatment of a hematological malignancy. In a particular embodiment, the invention relates to the use of a combination comprising the compound of formula (I) or a pharmaceutically acceptable salt thereof, and one or more therapeutic agents selected from tretinoin, cytarabine, pinometostat, EPZ-00477, Vorinostat, Ricolinostat, Entinostat, decitabine, azacitidine, Quizartinib, ABT-737, Nutlin-3A, dasatinib, JQ1, daunorubicin, arsenic trioxide, hydroxyurea, and pharmaceutically acceptable salts thereof for the preparation of medicaments useful in the treatment of a hematological malignancy disorder. In certain embodiments, said hematological malignancy is a myeloid hematological malignancy. In certain embodiments, said hematological malignancy is a lymphoid hematological malignancy.

Another embodiment relates to a combination as described herein and one or more pharmaceutically acceptable excipient.

Another embodiment relates to a combination as described herein for use as therapeutically active substance.

Another embodiment relates to a combination as described herein for use in the treatment of a hematological malignancy. In certain embodiments, said hematological malignancy is a myeloid hematological malignancy. In certain embodiments, said hematological malignancy is a lymphoid hematological malignancy.

Another embodiment relates to a method for the treatment of a hematological malignancy, which method comprises administering an effective amount of a combination as described herein to a human being or animal. In certain embodiments, said hematological malignancy is a myeloid hematological malignancy. In certain embodiments, said hematological malignancy is a lymphoid hematological malignancy.

Another embodiment relates to the use of a combination as described herein for the treatment of a hematological malignancy. In certain embodiments, said hematological malignancy is a myeloid hematological malignancy. In certain embodiments, said hematological malignancy is a lymphoid hematological malignancy.

Another embodiment relates to the use of a combination as described herein for the preparation of medicaments useful in the treatment of a hematological malignancy. In certain embodiments, said hematological malignancy is a myeloid hematological malignancy. In certain embodiments, said hematological malignancy is a lymphoid hematological malignancy.

In certain embodiments, the hematological malignancy is related to LSD1 or is modulated by LSD1 inhibitors.

In certain embodiments, the hematological malignancy is a myeloid hematological malignancy.

In certain embodiments, the hematological malignancy is acute myeloid leukemia (AML).

In certain embodiments, the hematological malignancy is a lymphoid hematological malignancy.

In certain embodiments, the hematological malignancy is acute lymphoid leukemia (ALL).

In certain embodiments, the combination comprises a compound of formula (I) or a pharmaceutically acceptable salt thereof and a retinoic acid analogue or a pharmaceutically acceptable salt thereof.

In certain embodiments, the combination comprises a compound of formula (I) or a pharmaceutically acceptable salt thereof and a nucleoside analogue or a pharmaceutically acceptable salt thereof.

In certain embodiments, the combination comprises a compound of formula (I) or a pharmaceutically acceptable salt thereof and a DOT1L inhibitor or a pharmaceutically acceptable salt thereof.

In certain embodiments, the combination comprises a compound of formula (I) or a pharmaceutically acceptable salt thereof and a HDAC inhibitor or a pharmaceutically acceptable salt thereof.

In certain embodiments, the combination comprises a compound of formula (I) or a pharmaceutically acceptable salt thereof and a DNMT inhibitor or a pharmaceutically acceptable salt thereof.

In certain embodiments, the combination comprises a compound of formula (I) or a pharmaceutically acceptable salt thereof and a FLT3 inhibitor or a pharmaceutically acceptable salt thereof.

In certain embodiments, the combination comprises a compound of formula (I) or a pharmaceutically acceptable salt thereof and a BCL2 inhibitor or a pharmaceutically acceptable salt thereof.

In certain embodiments, the combination comprises a compound of formula (I) or a pharmaceutically acceptable salt thereof and a MDM2 inhibitor or a pharmaceutically acceptable salt thereof.

In certain embodiments, the combination comprises a compound of formula (I) or a pharmaceutically acceptable salt thereof and a c-KIT inhibitor or a pharmaceutically acceptable salt thereof.

In certain embodiments, the combination comprises a compound of formula (I) or a pharmaceutically acceptable salt thereof and a BET inhibitor or a pharmaceutically acceptable salt thereof.

In certain embodiments, the combination comprises a compound of formula (I) or a pharmaceutically acceptable salt thereof and an anthracycline or a pharmaceutically acceptable salt thereof.

In certain embodiments, the combination comprises a compound of formula (I) or a pharmaceutically acceptable salt thereof and arsenic trioxide.

In certain embodiments, the combination comprises a compound of formula (I) or a pharmaceutically acceptable salt thereof and hydroxyurea.

In certain embodiments, the combination comprises a compound of formula (I) or a pharmaceutically acceptable salt thereof and tretinoin or a pharmaceutically acceptable salt thereof.

In certain embodiments, the combination comprises a compound of formula (I) or a pharmaceutically acceptable salt thereof and cytarabine or a pharmaceutically acceptable salt thereof.

In certain embodiments, the combination comprises a compound of formula (I) or a pharmaceutically acceptable salt thereof and pinometostat or a pharmaceutically acceptable salt thereof.

In certain embodiments, the combination comprises a compound of formula (I) or a pharmaceutically acceptable salt thereof and EPZ-004777 or a pharmaceutically acceptable salt thereof.

In certain embodiments, the combination comprises a compound of formula (I) or a pharmaceutically acceptable salt thereof and vorinostat or a pharmaceutically acceptable salt thereof.

In certain embodiments, the combination comprises a compound of formula (I) or a pharmaceutically acceptable salt thereof and ricolinostat or a pharmaceutically acceptable salt thereof.

In certain embodiments, the combination comprises a compound of formula (I) or a pharmaceutically acceptable salt thereof and entinostat or a pharmaceutically acceptable salt thereof.

In certain embodiments, the combination comprises a compound of formula (I) or a pharmaceutically acceptable salt thereof and decitabine or a pharmaceutically acceptable salt thereof.

In certain embodiments, the combination comprises a compound of formula (I) or a pharmaceutically acceptable salt thereof and azacitidine or a pharmaceutically acceptable salt thereof.

In certain embodiments, the combination comprises a compound of formula (I) or a pharmaceutically acceptable salt thereof and quizartinib or a pharmaceutically acceptable salt thereof.

In certain embodiments, the combination comprises a compound of formula (I) or a pharmaceutically acceptable salt thereof and ABT-737 or a pharmaceutically acceptable salt thereof.

In certain embodiments, the combination comprises a compound of formula (I) or a pharmaceutically acceptable salt thereof and Nutlin-3A or a pharmaceutically acceptable salt thereof.

In certain embodiments, the combination comprises a compound of formula (I) or a pharmaceutically acceptable salt thereof and dasatinib or a pharmaceutically acceptable salt thereof.

In certain embodiments, the combination comprises a compound of formula (I) or a pharmaceutically acceptable salt thereof and imatinib or a pharmaceutically acceptable salt thereof.

In certain embodiments, the combination comprises a compound of formula (I) or a pharmaceutically acceptable salt thereof and JQ1 or a pharmaceutically acceptable salt thereof.

In certain embodiments, the combination comprises a compound of formula (I) or a pharmaceutically acceptable salt thereof and daunorubicin or a pharmaceutically acceptable salt thereof.

In certain embodiments, the combination comprises a compound of formula (I) or a pharmaceutically acceptable salt thereof and idarubicin or a pharmaceutically acceptable salt thereof.

In certain embodiments, the combination comprises a compound of formula (I) or a pharmaceutically acceptable salt thereof, cytarabine and an anthracycline, preferably selected from daunorubicin, idarubicin, and pharmaceutically acceptable salts thereof.

In certain embodiments, the pharmaceutically acceptable salt of the compound of formula (I) as described above is a di-hydrochloride salt.

In the methods according to the invention described herein, the patient is a human being or animal, preferably a human being.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The term "optional" or "optionally" denotes that a subsequently described event or circumstance can but need not occur, and that the description includes instances where the event or circumstance occurs and instances in which it does not.

"The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker[37]; and Eliel, E. and Wilen, S.[38]. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog[39]. The prefixes D and L or (+) and (−) are employed to designate the sign of rotation of plane-polarized light by the compound, with (−) or L designating that the compound is levorotatory. A compound prefixed with (+) or D is dextrorotatory.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "inhibitor" denotes a compound which competes with, reduces or prevents the binding of a particular ligand to a particular receptor or enzyme and/or which reduces or prevents the activity of a particular protein, e.g. of a receptor or an enzyme.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "animal" as used herein comprises human beings and non-human animals. In one embodiment, a "non-human animal" is a mammal, for example a rodent such as rat or a mouse.

In one embodiment, a non-human animal is a mouse.

The term "half maximal effective concentration" ($EC_{50}$) denotes the plasma concentration of a particular compound or molecule required for obtaining 50% of the maximum of a particular effect in vivo.

The term "therapeutically effective amount" (or "effective amount") denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms. The term "translocation" or "chromosome translocation" denotes a type of chromosome abnormality caused by rearrangement of parts between nonhomologous chromosomes. Translocations can be balanced (in an even exchange of material with no genetic information extra or missing) or unbalanced (where the exchange of chromosome material is unequal resulting in extra or missing genes). Chromosomal translocations can occur either in gametogenesis, due to errors in meiosis, or in cellular division of somatic cells, due to errors in mitosis. The former results in a chromosomal abnormality featured in all cells of the offspring, as in translocation carriers. Somatic translocations, on the other hand, result in abnormalities featured only in the affected cell line.

The term "rearrangement" or "chromosomal rearrangement" denotes a type of chromosome abnormality caused by a change in the structure of the native chromosome through deletions, duplications, inversions, or translocations. Rearrangements are caused by a breakage in the DNA double helices at two different locations, followed by a rejoining of the broken ends to produce a new chromosomal arrangement of genes, different from the gene order of the chromosomes before they were broken. "Complex chromosomal rearrangements" (CCR) denote structural chromosomal rearrangements with at least three breakpoints with exchange of genetic material between two or more chromosomes.

Another embodiment provides pharmaceutical compositions or medicaments comprising the combinations of the compound of formula (I) as described herein and a pharmaceutically acceptable excipient, as well as methods of using the compound of formula (I) to prepare such combinations, compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compound of formula (I) and the other therapeutic agent for use in the combinations as described herein as well as the pharmaceutical compositions as described herein may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compound of formula (I) and the other therapeutic agent for use in the combinations as described herein as well as the pharmaceutical compositions as described herein may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing the compound of formula (I) or the therapeutic agent as described herein or the combination as described herein and a pharmaceutically acceptable excipient. Suitable excipients are well known to those skilled in the art and are described in detail in, e.g., Ansel H. C. et al.[40], Gennaro A. R. et al.[41], and Rowe R. C.[42]. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at the compound of formula (I) and the other therapeutic agents as described herein can be administered can vary within wide limits and will, of course, be fitted to the individual requirements in each particular case.

As described herein, the compound of formula (I) is a highly potent active pharmaceutical ingredient (HPAPI). The anticipated daily dose is thus very low, i.e. lower than 10 mg per day. Accordingly, the drug load in a solid form will also be very low, i.e. less than 10 mg of API per 100 mg of tablet.

In general, in the case of oral administration a daily dosage of about 0.01 to 10 mg per person of the compound of formula (I) as described herein should be appropriate, although the above upper limit can also be exceeded when necessary.

The additional compound of the combination may be administered in amounts that are effective for the purpose intended. Suitable dosages for any of the above coadministered agents are those presently used and may be lowered due to the combined action (synergy) of the newly identified combinations, such as to increase the therapeutic index or mitigate toxicity or other side-effects or consequences.

An example of a suitable oral dosage form for a compound of formula (I) is a tablet comprising about 0.01 mg to 10 mg of a compound of formula (I) as described herein compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

The combinations as described herein may be administered as a simultaneous or sequential regimen. When administered sequentially, the combination may be administered in two or more administrations. The combined administration includes coadministration, using separate formulation, and consecutive administration in either order, wherein preferably there is a time period while both (or all) active agents simultaneously exert their biological activities. The combinations of the invention may also be administered as a single pharmaceutical composition comprising the compound of formula (I) and the other therapeutic agent(s).

In a particular embodiment of therapy, the combination may be combined with surgical therapy and radiotherapy. The amounts of the combination and the relative timings of administration will be selected in order to achieve the desired combined therapeutic effect.

The compounds may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. For local immunosuppressive treatment, the compounds may be administered by intralesional administration, including perfusing or otherwise contacting the graft with the inhibitor before transplantation.

It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

The combinations as described herein may be employed for the treatment of a hyperproliferative disease or disorder, particularly hematological malignancies. As used herein, hematological malignancies relates to myeloid hematological malignancies and lymphoid hematological malignancies. As used herein, myeloid hematological malignancies and lymphoid hematological malignancies also include pre-malignant myeloid or lymphoid hematological disorders and non-neoplastic or non-malignant myeloproliferative or lymphoproliferative disorders.

In particular, the combinations of the present invention can be used for the treatment or prevention of:

Myeloid hematological malignancies, such as acute myeloid leukemia (AML) (e.g. Erythroleukemia, acute megakaryoblastic leukemia, Acute eosinophilic leukemia, Acute basophilic leukemia, Acute myelomonocytic leukemia, acute myeloblastic leukemia); Chronic myelogenous leukemia; Myelodysplasic syndrome; Chronic myelomonocytic leukemia; and Myeloproliferative diseases (e.g. myelofibrosis, acute biphenotypic leukemia, Polycythemia vera, Chronic eosinophilic leukemia/Hypereosinophilic syndrome, Essential thrombocytosis, and Chronic eosinophilic leukemia/Hypereosinophilic syndrome)

Lymphoid Hematological malignancies, such as acute lymphoblastic leukemia (ALL), T-cell lymphoblastic leukemia/lymphoma In preferred embodiments, the combinations of the present invention are used for the treatment of myeloid hematological malignancies. In certain embodiments, the combinations of the invention are used for the treatment of acute myeloid leukemia. In certain embodiments, the combinations of the invention are preferentially used to treat myeloid or lymphoid hematological malignancies with translocation or rearrangements involving MLL, AF9, AF4, AF10, AML1, ETO, CALM; or mutation in NPM1 or Notch1, or LSD1 overexpression.

One particular embodiment of the invention relates to a method for the treatment of a hyperproliferative disorder, particularly a hematological malignancy, which method comprises sensitizing through administration of an LSD1 inhibitor followed by administering an effective amount of a combination as described herein to a human being or animal.

One particular embodiment of the invention relates to a method for the treatment of a hyperproliferative disorder, particularly a hematological malignancy, which method comprises sensitizing through administration of a compound of formula (I) or a pharmaceutically acceptable salt thereof followed by administering an effective amount of a combination as described herein to a human being or animal.

In another embodiment of the invention, an article of manufacture, or "kit", containing a combination useful for the treatment of the diseases and disorders described above is provided.

In one embodiment, the article of manufacture comprises a container and a combination described herein.

One embodiment of the invention provides an article of manufacture comprising a combination as described herein useful in the treatment of a hyperproliferative disorder, particularly a hematological malignancy.

The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a combination, or a formulation thereof, which is effective for treating the condition and may have a sterile access port (for example, the container may be an intravenous solution bag or a vial having a stopper pierceable by a hypodermic injection needle). The label or package insert indicates that the composition is used for treating the condition of choice, such as hyperproliferative disorders, particularly a hematological malignancy. In one embodiment, the label or package inserts indicates that the composition comprising the combination can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the combination, and, if present, the second pharmaceutical formulation. For example, if the kit comprises a first composition comprising a compound of formula (I), or a pharmaceutically acceptable salt thereof and a second pharmaceutical composition comprising one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof, the kit may further comprise directions for the simultaneous, sequential or separate administration of the first and second pharmaceutical compositions to a patient in need thereof.

In another embodiment, the kits are suitable for the delivery of solid oral forms of a combination, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of formula (I), or a pharmaceutically acceptable salt thereof contained therein; (b) a second container with one therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof and (c) a third container with a third pharmaceutical composition contained therein, wherein the third pharmaceutical formulation comprises another compound with anti-hyperproliferative activity selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof. Alternatively, or additionally, the kit may comprise another container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of a compound of formula (I), or a pharmaceutically acceptable salt thereof and one or more therapeutic agents selected from the group consisting of retinoic acid analogues, nucleoside analogues, DOT1L inhibitors, HDAC inhibitors, demethylating agents, FLT3 inhibitors, BCL2 inhibitors, MDM2 inhibitors, c-KIT inhibitors, BET inhibitors, anthracyclines, arsenic trioxide, hydroxyurea, and pharmaceutically acceptable salts thereof, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

The following examples are provided for illustration of the invention. They should not be considered as limiting the scope of the invention, but merely as being representative thereof.

Example 1: Matrix Assays for Determination of Synergy Between ORY-1001 and Other Therapeutic Agents in Acute Myeloid Leukemia Cell Lines The objective of this example is to determine synergism existing between ORY-1001 and other therapeutic agents. Table 1 summarizes the compounds tested in the combination therapy and cell the lines used.

TABLE 1

List of compounds that will be tested in combination with ORY-1001.

| Compound | Class | Cell lines |
|---|---|---|
| ATRA | RA analogue | MV(4; 11), MOLM-13 |
| ARAC | Nucleotide analogue | MV(4; 11), MOLM-13, OCI-AML3 |
| EPZ5676 | DOT1L inhibitor | MV(4; 11), MOLM-13 |
| SAHA | HDAC inhibitor | MV(4; 11), MOLM-13 |
| Rocilinostat* | HDAC inhibitor | MV(4; 11), MOLM-13, OCI-AML3 |
| Azacitidine | Demethylating agent | MV(4; 11), MOLM-13 |
| Decitabine | Demethylating agent | MV(4; 11), MOLM-13 |
| Quizartinib | FLT3 inhibitor | MV(4; 11), MOLM-13 |
| ABT737 | BCL2 inhibitor | MV(4; 11), MOLM-13 |
| Nutlin3A | MDM2 inhibitor | MOLM-13 |

*Also known as Ricolinostat and ACY-1215.

1.1 Experimental Design
1.1.1 Cell Lines and Culture Conditions

AML cell lines were maintained in RPMI 10% FBS medium at 37° C. in a humidified incubator with controlled 5% $CO_2$ atmosphere. Cell freezing and thawing was performed following recommendation from ATCC. Genetic profiling of the cell lines used is available in table 2.

TABLE 2

Genetic characterization of the AML cell lines reported in this document.

| Cell lines | Tissue of origin | Mutational status |
|---|---|---|
| THP1 | Acute monocytic leukaemia (M5b) | MLL-AF9 rearraged |
| MV4-11 | Acute monocytic leukaemia (M5b) | MLL-AF4 rearranged, FLT3-ITD |
| OCI-AML3 | Acute myelomonocitic leukaemia (M4) | MLL wt, NPM1 mut, DNMT3a mut |

TABLE 2-continued

Genetic characterization of the AML cell lines reported in this document.

| Cell lines | Tissue of origin | Mutational status |
|---|---|---|
| OCI-AML2 | Acute myelomonocitic leukaemia (M4) | MLL wt, NPM1 wt, DNMT3a mut |
| MOLM13 | Acute monoblastic leukaemia (M5a) | MLL-AF9, FLT3-ITD |
| HL60 | Acute promyelocytic leukaemia | MLL wt, Myc amplification |
| KASUMI1 | Acute myeloid leukaemia | MLL wt, AML-ETO rearranged |

1.1.2 Viability Assays (96 Hours)

Cells were seeded at the optimal density (to guarantee linear growth during the treatment), as previously determined (4000 cells/well, except 16000 cells/well in the case of KASUMI-1 cells), in 96-well plates with 50 μL of medium. Three wells were reserved for each experimental condition; medium-only and vehicle-treated controls were also added for background correction and normalization respectively. After seeding, 50 μL of medium containing 8 serial dilutions (1:3) of ORY-1001 (or any other candidates for combinatorial treatment) were added to the cells. Cells were then incubated for 96 hours at 37° C. in a controlled 5% $CO_2$ atmosphere, prior to evaluate cell viability using Alamar Blue® (ThermoFisher Scientific, Waltham, Mass./USA) viability staining. Alamar Blue® is a cell viability indicator that uses the natural reducing power of living cells to convert resazurin to the fluorescent molecule, resorufin[43]. Briefly, Alamar Blue stock solution was diluted 1:20 in the culture medium and, after 3 hours incubation, fluorescence was detected using a TECAN Infinity 2000 plate reader (Tecan Group Ltd., Männedorf, C H; 540-570 nm excitation wavelength, 580-610 nm emission wavelength). For each condition, the average fluorescence was calculated from 3 technical replicates; background correction was calculated from the fluorescence of medium-only controls. Data were analyzed using the GraphPad PRISM® version 5.01 (GraphPad Software, Inc., La Jolla, Calif./USA) to calculate the best-fitting curve and the $EC_{50}$ value.

1.1.3 9×9 Matrix Viability Assays

Each matrix assay was distributed across 2 plates following the scheme illustrated below in FIG. 1.

Cells were seeded at the optimal density (4000 cells/wells, as previously determined) in 96-well plates with 50 μL of medium; the wells at edges of the plates were left with 100 μL of medium without cells, for background correction. Each of the two compounds was added in 25 μL, resulting in a final volume of 100 μL of medium. As shown in FIG. 1, the matrix was designed with increasing concentrations of ORY-1001 from left to right and increasing concentrations of the compound of interest (see table 1) from top to the bottom. The first and the last row of plate #1 have been repeated in plate #2 (indicated by red arrows in FIG. 1), to confirm reproducibility across the two plates. The concentrations tested for both the compounds were covering a 256-folds range obtained through 8 1:2 dilutions steps, designed to have the $EC_{50}$s of both the compounds centered horizontally and vertically on the matrix (the $EC_{50}$s of ORY-1001 and the other compound correspond to the 5th well from the right and from the bottom, as indicated in FIG. 1). The $EC_{50}$ values for the compounds tested in the matrix assays were previously obtained through single agent assays performed as detailed in the section 1.1.2. For compounds in which a wide concentration range was tested (Decitabine, Azacitidine and Nutlin3A) serial dilutions were performed in 1:3 steps.

Viability was then determined using Alamar Blue staining as detailed in the section 1.1.2.

1.1.3.1 9×9 Matrix Viability Assays (Data Analysis)

For each matrix assay, data were then normalized against the vehicle-treated controls (<0.4% DMSO, in the upper left corner) to obtain the percentage value of relative viability, according to the following formula:

% relative viability=RFU treated cells/RFU vehicle control×100

The values of percentage viability were then analyzed using GraphPad PRISM® version 5.01 (GraphPad Software, Inc., La Jolla, Calif./USA) to calculate the best-fitting curve and the $EC_{50}$ values.

At this point the Fraction affected (Fa) was calculated using the formula

Fa=1−(% relative viability/100)

for the following conditions:

Cells treated with serial dilutions of ORY-1001 as single agent (average of the first row of the first and second plate of each matrix assay)

Cells treated with serial dilutions of the compound of interest as single agent (in the first column of the matrix assay)

Cell treated with ORY-1001 and the compound of interest at a fixed ratio corresponding to the ratio of $EC_{50}$ values (values of % relative viability in the diagonal of the matrix assay; highlighted in FIG. 1).

The Fa values previously described were then averaged across the two technical duplicates, before analysis with Calcusyn.

The Calcusyn software (http://www.biosoft.com/w/calcusyn.htm, Biosoft, Cambridge, UK) is designed to determine the nature (synergistic, additive or antagonistic) of the interaction between two compounds, on the basis of the Median Effect Principle and the Combination Index Theorem[44]. In order to generate informative results, the data that are going to be processed with Calcusyn (both for the single agents and the drug combination) need to fit with these theoretical models. For this reason, it is crucial to remove possible outliers and data points characterized by poor fit to the Median Effect Principle[45]. In order to achieve this, the following strategy was adopted for data filtering.

In the first step data dispersion was reduced removing points characterized by:

1) Fa<0.1
2) Increase in Fa<0.03, compared to the previous point (if Fa>0.9).

These conditions define the plateaus of the dose response curve, in which cells have been treated with very low or very high concentrations of compounds (or combos), resulting in reduction of viability close to 0% or 100% (equivalent to Fa value close to 0 or 1 respectively). To be noted that in these areas of the dose-response curve the changes in Alamar Blue signal are very small and most likely the result of random noise with very little biological significance.

Next, for each data point, $\text{Log}_{10}$(Concentration) and $\text{Log}_{10}$(Fa/(1−Fa)) were calculated and a dot plot graph was generated reporting the former value on the x axis and the latter on the y axis. With Excel, a regression line was then obtained (corresponding to the Median Effect Equation).

At this point the distance from the regression line was calculated for each data point with the equation:

$$\text{Distance}(ax+by+c=0;X,Y)=(aX+bY+c)/\sqrt{(a^2+b^2)}$$

Outliers are identified on the basis of their distance from the Median Effect Equation, using the Grubbs test. For each data point, the Grubbs test was performed on the absolute value of the distance, according to the following formula (to be noted that the variable for the Grubbs test can be called interchangeably G or Z):

$$G=(X_n-X_{average})/s$$

Where $X_n$ stands for the absolute value of the distance of each points from the regression line; $X_{average}$ stands for average of all the $X_n$ values and s stands for the standard deviation. Values of G above $G_{crit}$ (calculated for α=0.2 as shown below) identify outliers not fitting on the Median Effect Equation. Such data points have been removed to successfully calculate the Combination Index with Calcusyn.

$$G_{crit} = \frac{(n-1)t_{crit}}{\sqrt{n(n-2+t_{crit}^2)}}$$

When possible, the test was reiterated more than once to remove multiple outliers, until:

1. no further outliers were identified or
2. $R^2 > 0.95$. To measure data quality, the R value is calculated also by the Calcusyn software (good data are characterized by R value above 0.95[46].

1.1.3.2 Calcusyn Output

On the x axis is reported the Fractional Effect (also called Fraction Affected referred in the text as Fa), representing the fraction of cells affected by the treatment (in the case of a cytotoxic treatment the Fractional Effect corresponds to viability reduction compared to vehicle controls, where 1 is equal to 100%). On the y axis is reported the combination index, which can be either synergistic (CI<1), additive (CI=1) or antagonistic (CI>1). The crosses stand for the experimental data points, the central line is the CI curve, the upper and the lower lines define the range of 1.96 standard deviations (SD) above and below the CI.

1.1.4 Combinatorial Treatments Dasatinib/ORY-1001 and JQ1/ORY-1001

Cells were seeded at the density of 2500 cells/well in 96-well plates with 50 μL of medium; the wells at edges of the plates were left with 100 μL of medium without cells, for background correction. Each of the two compounds was added in 25 μL, resulting in a final volume of 100 μL of medium. Cells were treated with serial 1:3 dilution of both ORY-1001 and either Dasatinib or JQ-1. The ratio ORY-1001/Dasatinib and ORY-1001/JQ1 was respectively 1:1000 and 1:200.

Viability was then determined using Alamar Blue staining as detailed in the section 1.1.2.

1.1.4.1 Combinatorial Treatments Dasatinib/ORY-1001 and JQ1/ORY-1001 (Data Analysis)

Data analysis was performed as described in the section 1.1.3.1.

1.1.4.2 Calcusyn Output

Output of the Calcusyn software as described in the section 1.1.3.2.

1.1.5 Combinatorial Treatment ORY-1001/Hydroxyurea

Cells were seeded at the density of 4000 cells/well in 96-well plates with 50 μL of medium; the wells at edges of the plates were left with 100 μL of medium without cells, for background correction. Each of the two compounds was added in 25 μL, resulting in a final volume of 100 μL of medium. Cells were treated with serial 1:3 dilution of Hydroxyurea in presence of a fixed concentration of either ORY-1001 (5 nM) or vehicle (0.05%).

Viability was then determined using Alamar Blue staining as detailed in the section 1.1.2. Data were analyzed using the GraphPad PRISM® version 5.01 (GraphPad Software, Inc., La Jolla, Calif./USA) to calculate the best-fitting curve and the $EC_{50}$ value.

1.1.6 Combinatorial Treatment ORY-1001/$As_2O_3$

Cells were seeded at the density of 2500 cells/well in 96-well plates with 50 μL of medium; the wells at edges of the plates were left with 100 μL of medium without cells, for background correction. Each of the two compounds was added in 25 μL, resulting in a final volume of 100 μL of medium. Cells were treated with serial 1:3 dilution of $AsO_3$ in presence of a fixed concentration of either ORY-1001 (5 nM) or vehicle (0.05%).

Viability was then determined using Alamar Blue staining as detailed in the section 1.1.2. Data were analyzed using the GraphPad PRISM® version 5.01 (GraphPad Software, Inc., La Jolla, Calif./USA) to calculate the best-fitting curve and the $EC_{50}$ value.

1.2 Results 1.2.1 ORY-1001 Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of ORY-1001 (range from 0.015 to 100 nM) as described in the section 1.1.2. With the exception of OCI-AML2, in the AML cell lines tested, ORY-1001 induced a reduction of viability greater than 20% (compared to vehicle controls), with $EC_{50}$ values in the sub-nanomolar range.

1.2.2 ATRA Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of ATRA (range from 0.015 to 100 nM) as described in the section 1.1.2. Reduction of viability greater than 20% (compared to vehicle controls) was detected in the THP-1 ($EC_{50}$=1.7 nM), MV(4;11) ($EC_{50}$=2.8 nM), HL-60 ($EC_{50}$=2.7 nM), OCI-AML2 ($EC_{50}$=5.9 nM), OCI-AML3 ($EC_{50}$=0.8 nM) and MOLM-13 cells ($EC_{50}$=4.8 nM).

1.2.2.1 Combination ORY-1001/ATRA

Figure 2A:
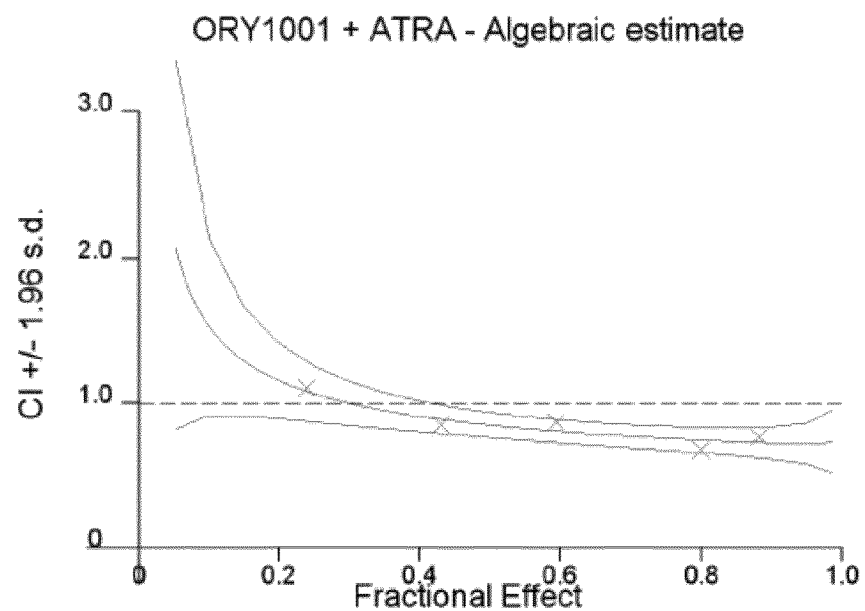
FIG. 2: Combination indexes calculated for the combo ORY-1001/ATRA in MV(4;11) (FIG. 2A) and MOLM-13 cells (FIG. 2B) following the procedure described in Example 1.2.2.1.
Figure 2B:
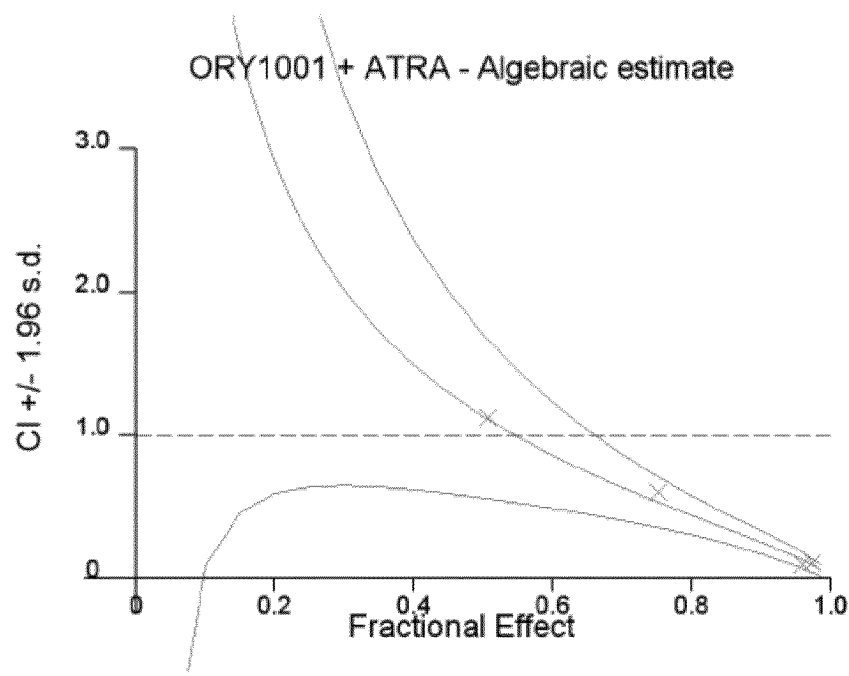

Matrix treatments with ATRA (0.16-40 nM) and ORY-1001 (0.006-1.6 nM) were performed on MV(4;11) and MOLM-13 cells as described in the section 1.1.3. Data analysis and calculation of combination indexes as reported in 1.1.3.1. The results obtained are shown in FIGS. 2A and 2B.

In the conditions tested, synergy (CI<1) was detected between ORY-1001 and ATRA at Fa value above 0.5 in MV(4;11) cells (n=2) and 0.8 in MOLM-13 cells (n=2).

1.2.3 ARA-C Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of ARA-C (range from 0.15 to 1000 nM) as described in the section 1.1.2. Reduction of viability greater than 20% (compared to vehicle controls) was detected in the THP-1 (EC50=251.7 nM), MV(4;11) (EC50=198 nM), HL-60 (EC50=43.5 nM), OCI-AML2 (EC50=26.5 nM), OCI-AML3 (EC50=144.8 nM), KASUMI-1 (EC50=28.7 nM) and MOLM-13 cells (EC50=78.5 nM).

1.2.3.1 Combination ORY-1001/ARA-C

Figure 3A:
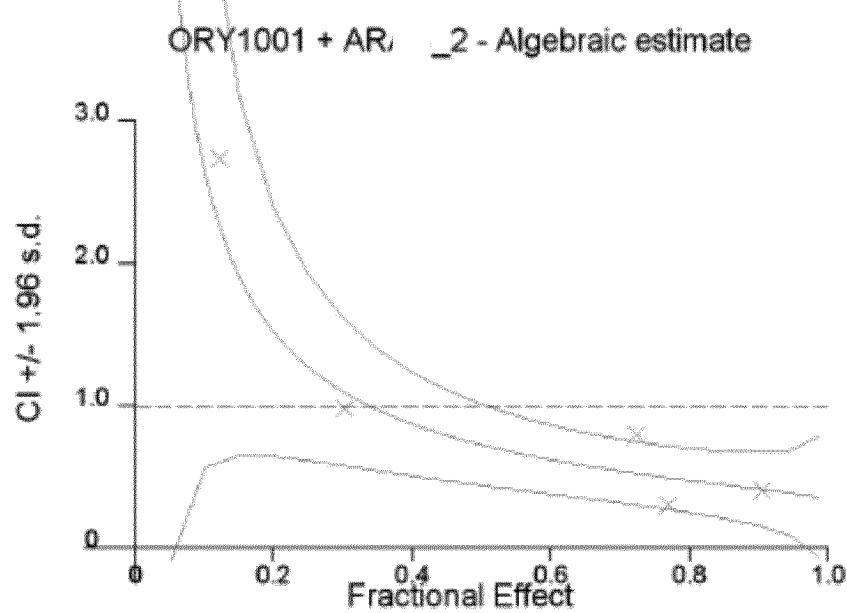
FIG. 3: Combination indexes calculated for the combo ORY-1001/ARA-C in MV(4;11) (FIG. 3A), OCI-AML3 (FIG. 3B) and MOLM-13 cells (FIG. 3C) following the procedure described in Example 1.2.3.1.
Figure 3B:
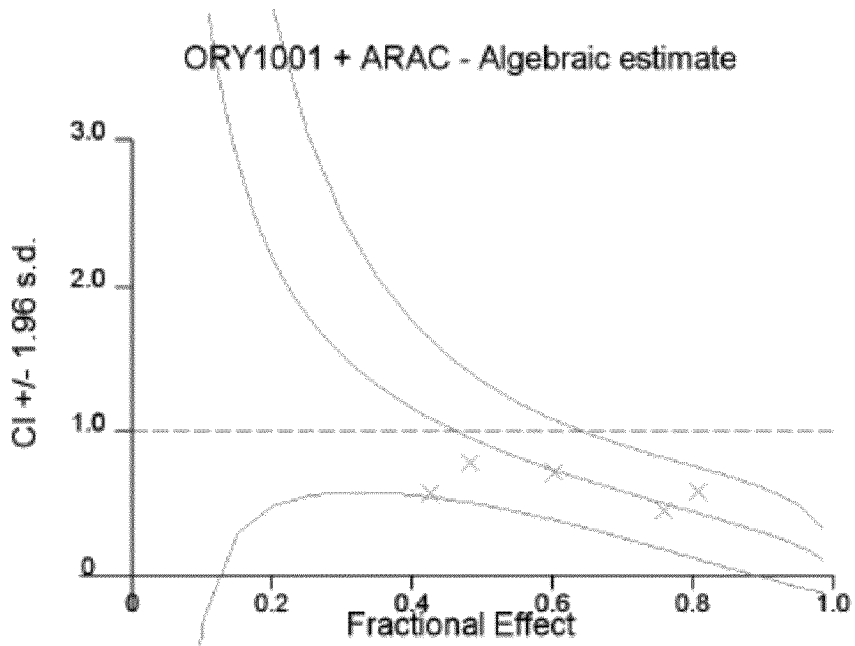
Figure 3C:
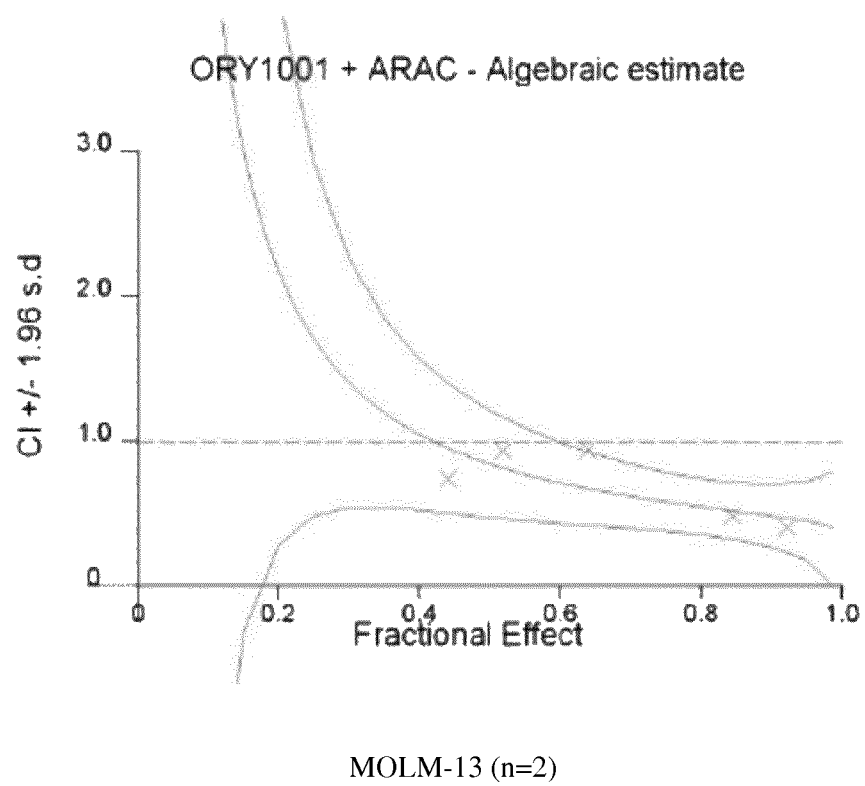

Matrix treatments with ARA-C (6.25-1600 nM) and ORY-1001 (0.006-1.6 nM) were performed on MV(4-11), OCI-AML3 and MOLM-13 cells as described in the section 1.1.3. Data analysis and calculation of combination indexes as reported in 1.1.3.1. The results obtained are shown in FIGS. 3A, 3B and 3C.

In the conditions tested, ORY-1001 synergistically enhances the response of MV(4;11) cells to ARA-C for Fa>0.5 (n=1). In OCI-AML3 and MOLM-13 cells synergy between ARA-C and ORY-1001 was detected at Fa>0.7 and Fa>0.6 respectively (n=2).

1.2.4 EPZ5676 Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of EPZ5676 (range from 1.5 nM to 10 µM) as described in the section 1.1.2. Reduction of viability greater than 20% (compared to vehicle controls) was detected in MV(4;11) ($EC_{50}$=16 nM) and MOLM-13 cells ($EC_{50}$=44.7 nM).

1.2.4.1 Combination ORY-1001/EPZ5676

Figure 4A:
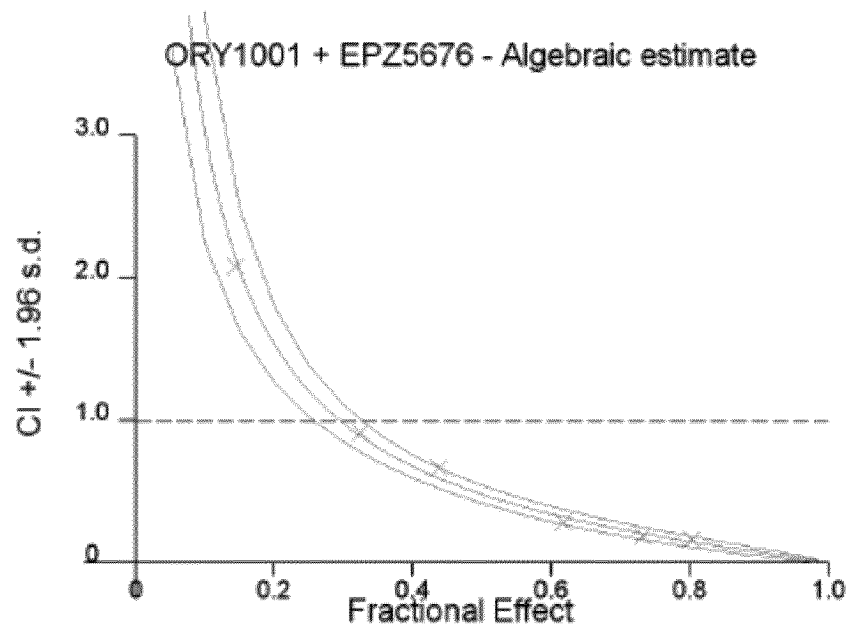
FIG. 4: Combination indexes calculated for the combo ORY-1001/EPZ5676 in MV(4;11) (FIG. 4A) and MOLM-13 cells (FIG. 4B) following the procedure described in Example 1.2.4.1.
Figure 4B:
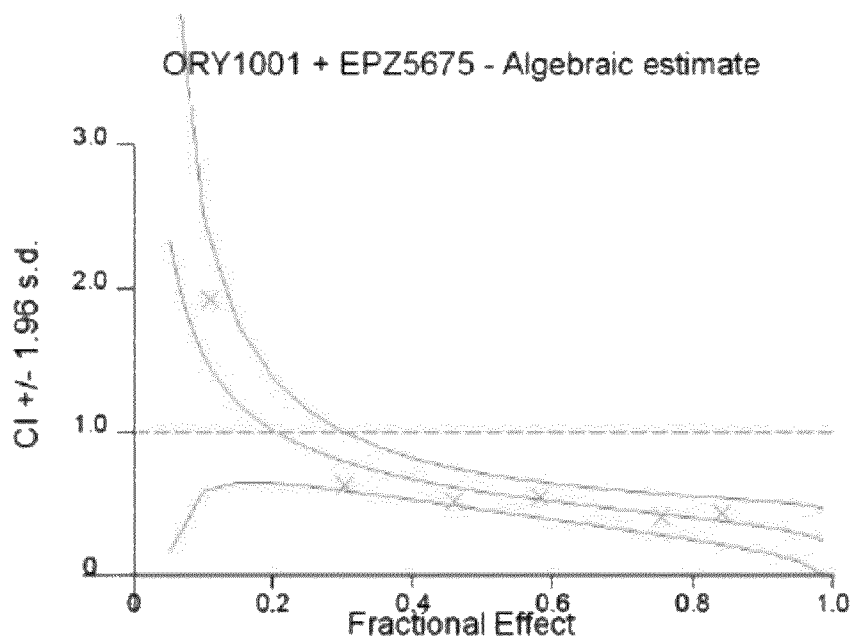

Matrix treatments with EPZ5676 (1.25-320 nM) and ORY-1001 (0.006-1.6 nM) were performed on MV(4;11) and MOLM-13 cells as described in the section 1.1.3. Data analysis and calculation of combination indexes as reported in 1.1.3.1. The results obtained are shown in FIGS. 4A and 4B.

In the conditions tested, synergy between ORY-1001 and EPZ56756 was detected at Fa>0.4 in MV(4;11) cells (n=2) and at Fa>0.3 in MOLM-13 cells (n=2).

1.2.5 EPZ004777 Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.2%) or serial 1:3 dilution of EPZ004777 (range from 2.5 nM to 16.7 µM) as described in the section 1.1.2. Reduction of viability greater than 20% (compared to vehicle controls) was detected in MV(4;11) ($EC_{50}$=118 nM) and MOLM-13 cells ($EC_{50}$=108.3 nM).

1.2.6 SAHA Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of SAHA (range from 1.5 nM to 10 µM) as described in the section 1.1.2. Reduction of viability greater than 20% (compared to vehicle controls) was detected in the THP-1, MV(4;11), HL-60, OCI-AML2, OCI-AML3, KASUMI-1 and MOLM-13 cells ($EC_{50}$ in the 100-1000 nM range).

1.2.6.1 Combination ORY-1001/SAHA

Figure 5A:
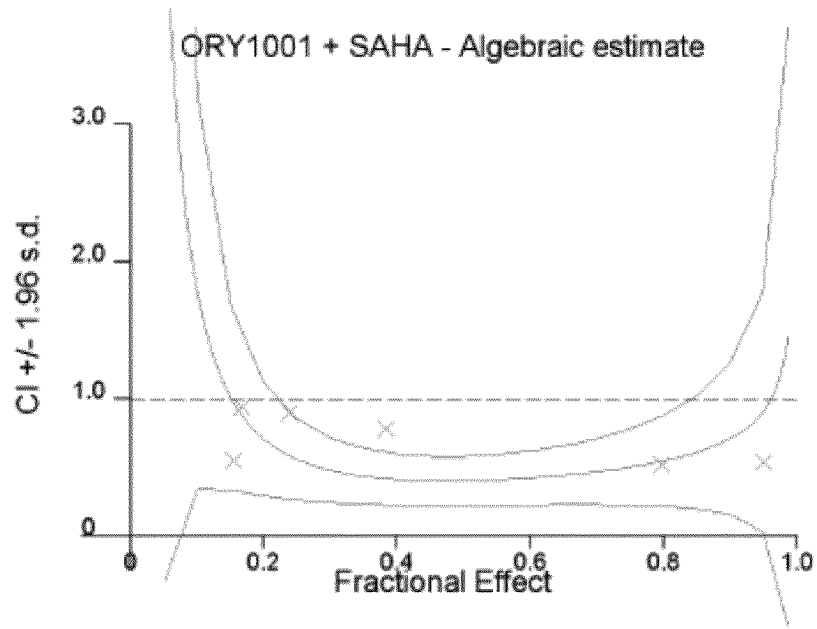
FIG. 5: Combination indexes calculated for the combo ORY-1001/SAHA in MV(4;11) (FIG. 5A) and MOLM-13 cells (FIG. 5B) following the procedure described in Example 1.2.6.1.
Figure 5B:
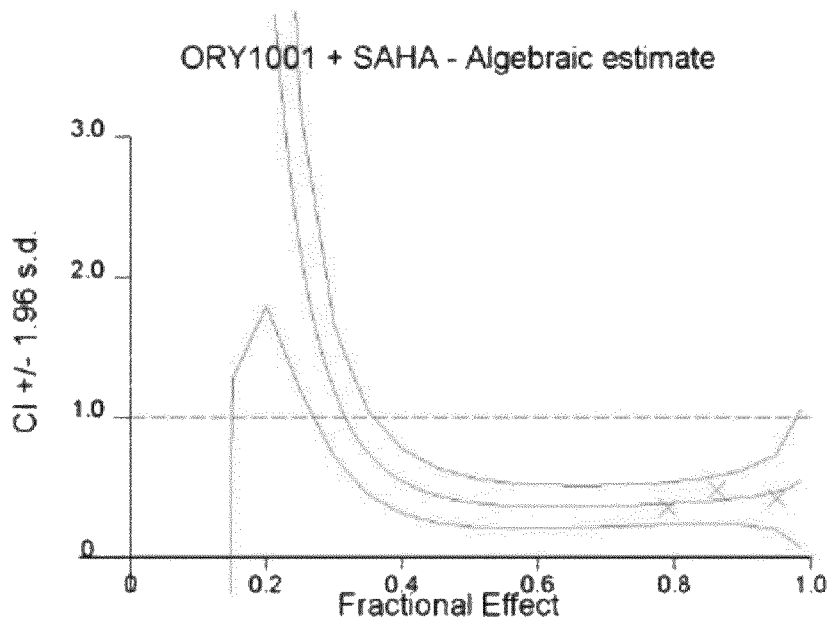

Matrix treatments with SAHA (6.25-1600 nM) and ORY-1001 (0.006-1.6 nM) were performed on MV(4;11) and MOLM-13 cells as described in the section 1.1.3. Data analysis and calculation of combination indexes as reported in 1.1.3.1. The results obtained are shown in FIGS. 5A and 5B.

In the conditions tested, synergistic interaction between ORY-1001 and SAHA was detected in MV(4;11) at Fa values between 0.3 and 0.8 (n=2) and in MOLM-13 cells at Fa>0.4 (n=1).

1.2.7 Rocilinostat Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of Rocilinostat (range from 1.5 nM to 10 µM) as described in the section 1.1.2. Reduction of viability greater than 20% (compared to vehicle controls) was detected in the THP-1, MV(4;11), HL-60, OCI-AML2, OCI-AML3, KASUMI-1 and MOLM-13 cells ($EC_{50}$ in the 0.5-3 µM range).

1.2.7.1 Combination ORY-1001/Rocilinostat

Figure 6A:
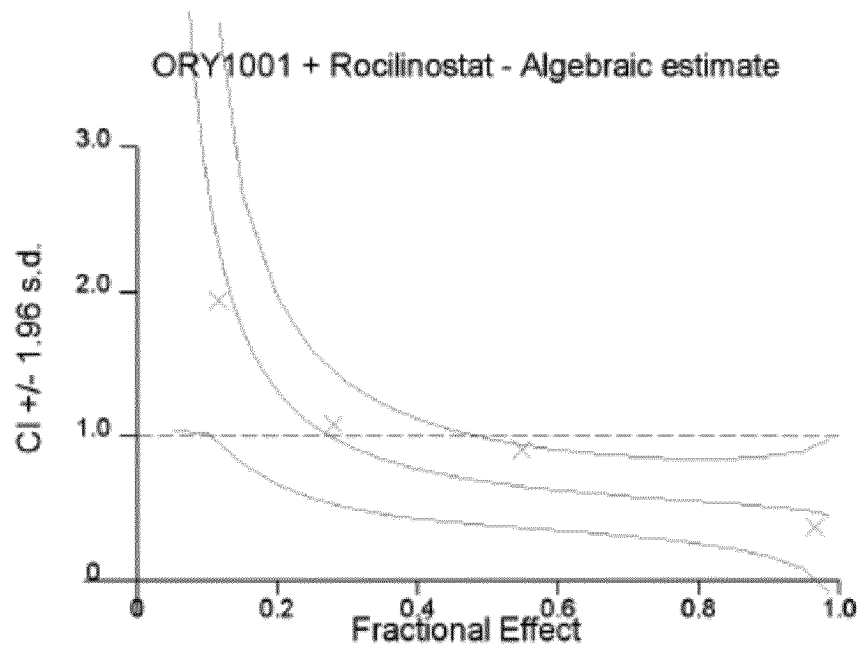
FIG. 6: Combination indexes calculated for the combo ORY1001/Rocilinostat in MV(4;11) (FIG. 6A), OCI-AML3 (FIG. 6B) and MOLM-13 cells (FIG. 6C) following the procedure described in Example 1.2.7.1.
Figure 6B:
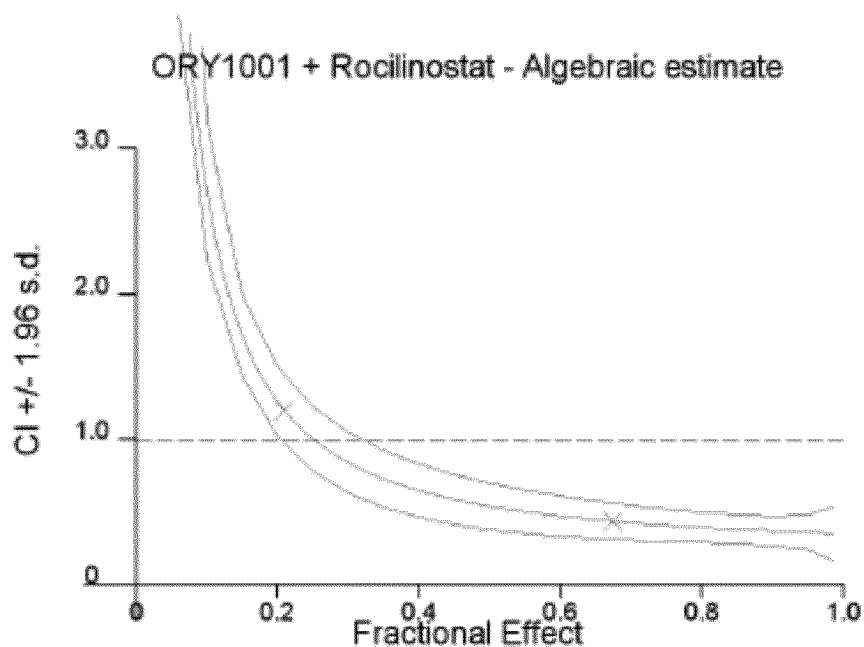
Figure 6C:
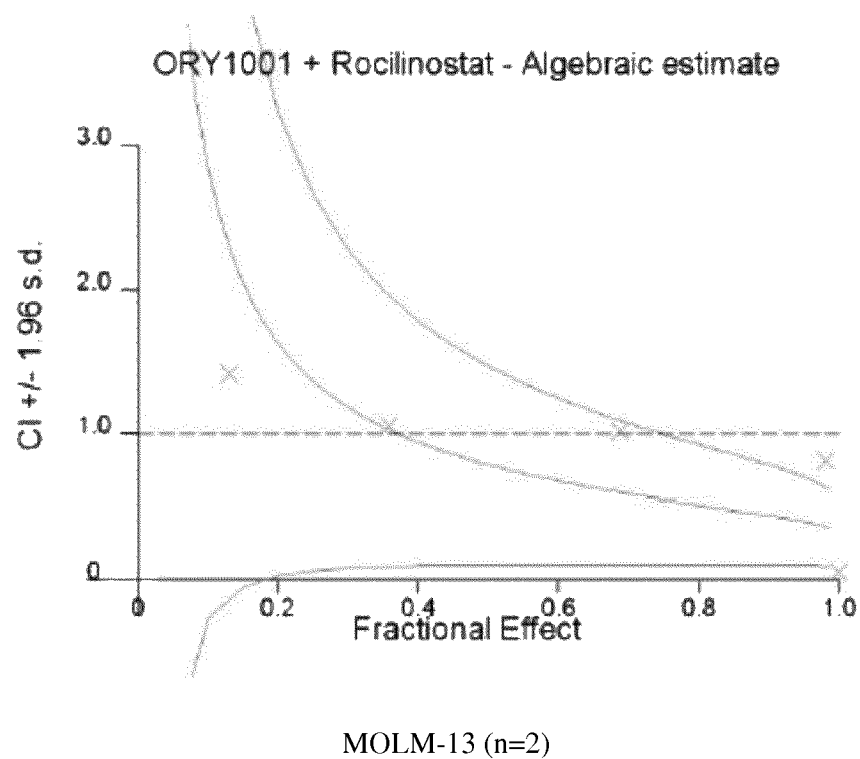

Matrix treatments with Rocilinostat (15.6-4000 nM) and ORY-1001 (0.006-1.6 nM) were performed on MV(4;11), OCI-AML3 and MOLM-13 cells as described in the section 1.1.3. Data analysis and calculation of combination indexes as reported in 1.1.3.1. The results obtained are shown in FIGS. 6A, 6B and 6C.

In the conditions tested, ORY-1001 interacts synergistically with Rocilinostat at Fa>0.6 in MV(4;11) cells (n=2) and Fa>0.4 in OCI-AML3 cells (n=2). In MOLM-13 cells synergy was detected for Fa>0.8 (n=2).

1.2.8 Entinostat Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.1%) or serial 1:3 dilution of Entinostat (range from 7.6 nM to 50 µM) as described in the section 1.1.2. Reduction of viability greater than 20% (compared to vehicle controls) was detected in the THP-1 ($EC_{50}$=230 nM), MV(4;11) ($EC_{50}$=98.5 nM), HL-60 ($EC_{50}$=42 nM), OCI-AML2 ($EC_{50}$=106.5 nM), OCI-AML3 ($EC_{50}$=55.2 nM), KASUMI-1 ($EC_{50}$=167.5 nM) and MOLM-13 cells ($EC_{50}$=52 nM).

1.2.9 Azacitidine Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of Azacitidine (range from 15 nM to 100 µM) as described in the section 1.1.2. Reduction of viability greater than 20% (compared to vehicle controls) was detected in the THP-1 ($EC_{50}$=2881.5 nM), MV(4;11) ($EC_{50}$=1112 nM), HL-60 ($EC_{50}$=1812 nM), OCI-AML2 ($EC_{50}$=1851.7 nM), OCI-AML3 ($EC_{50}$=889.4 nM), KASUMI-1 ($EC_{50}$=2281.7 nM) and MOLM-13 cells ($EC_{50}$=322.8 nM).

1.2.9.1 Combination ORY-1001/Azacitidine

Figure 7A:
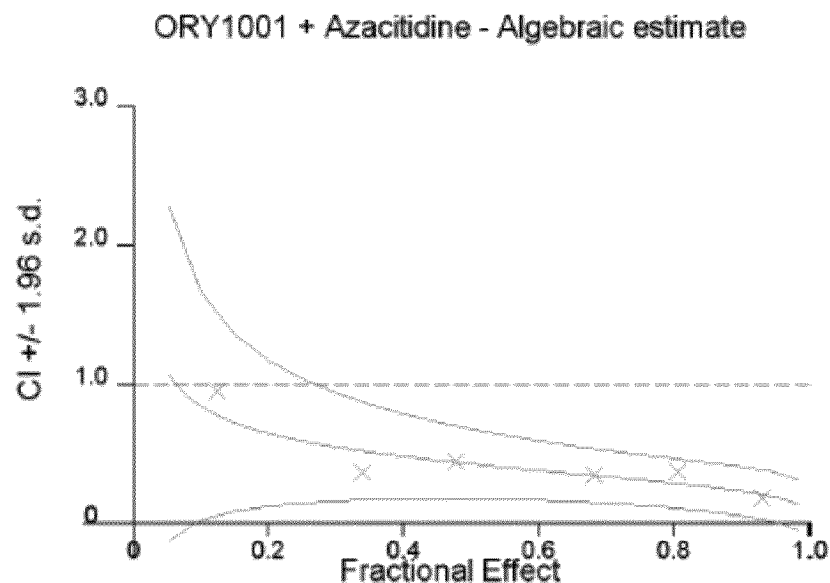
FIG. 7: Combination indexes calculated for the combo ORY-1001/Azacitidine in MV(4;11) (FIG. 7A) and MOLM-13 cells (FIG. 7B) following the procedure described in Example 1.2.9.1.
Figure 7B:
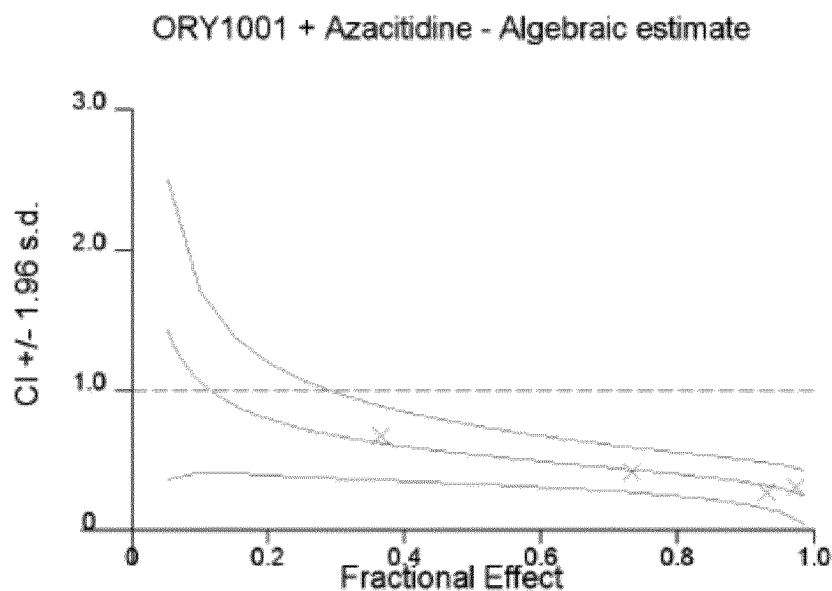

Matrix treatments with Azacitidine (9.5 nM-62.3 µM) and ORY-1001 (0.001-8 nM) were performed on MV(4;11) and MOLM-13 cells as described in the section 1.1.3. Data analysis and calculation of combination indexes as reported in 1.1.3.1. The results obtained are shown in FIGS. 7A and 7B.

In the conditions tested, in both MV(4;11) and MOLM-13 cells ORY-1001 synergizes with Azacitidine at Fa>0.3 (n=2).

1.2.10 Decitabine Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of Decitabine (range from 1.5 nM to 10 µM) as described in the section 1.1.2. Reduction of viability greater than 20% (compared to vehicle controls) was detected in the THP-1 ($EC_{50}$=95 nM), MV(4;11) ($EC_{50}$=79.5 nM), HL-60 ($EC_{50}$=42.1 nM), OCI-AML2 ($EC_{50}$=36 nM), OCI-AML3 ($EC_{50}$=100.5 nM), KASUMI-1 ($EC_{50}$=24 nM) and MOLM-13 cells ($EC_{50}$=12.6 nM).

1.2.10.1 Combination ORY-1001/Decitabine

Figure 8A:
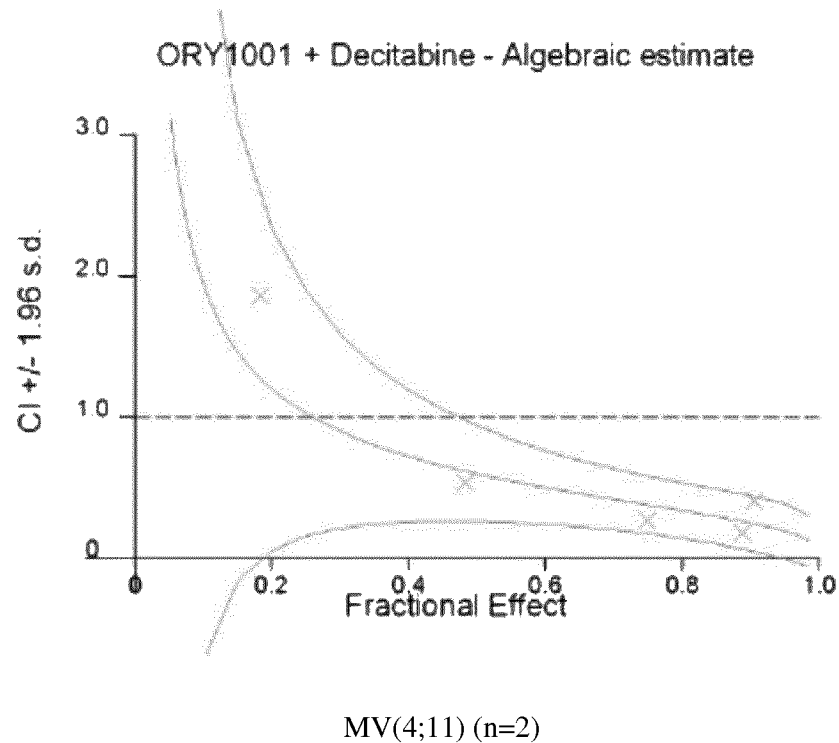
FIG. 8: Combination indexes calculated for the combo ORY-1001/Decitabine in MV(4;11) (FIG. 8A) and MOLM-13 cells (FIG. 8B) following the procedure described in Example 1.2.10.1.
Figure 8B:
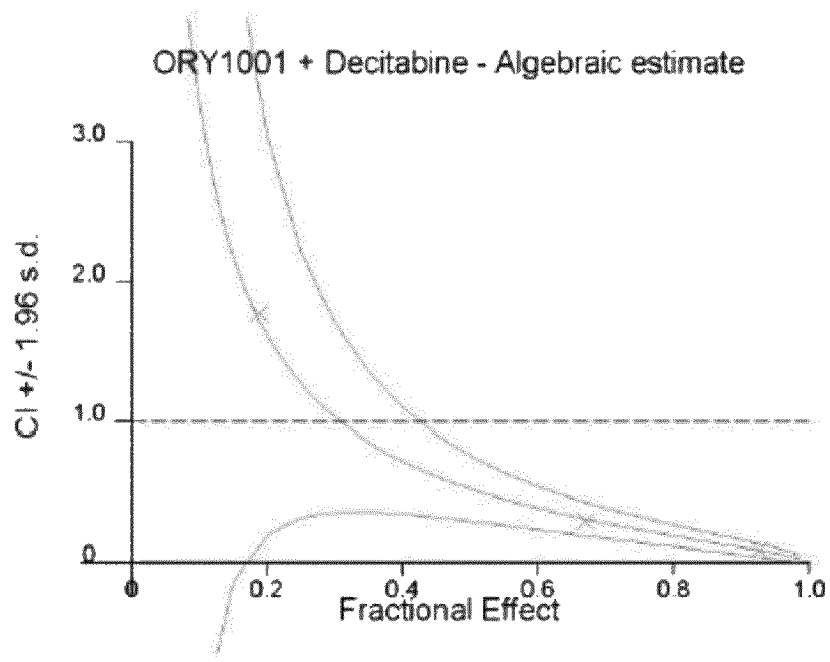

Matrix treatments with Decitabine (0.4-2430 nM) and ORY-1001 (0.004-24.3 nM) were performed on MV(4;11) and MOLM-13 cells as described in the section 1.1.3. Data analysis and calculation of combination indexes as reported in 1.1.3.1. The results obtained are shown in FIGS. 8A and 8B.

In the conditions tested, synergistic effect between ORY-1001 and Decitabine was detected for Fa>0.5 (n=2) in both MV(4;11) and MOLM-13 cells.

1.2.11 Quizartinib Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.1%) or serial 1:3 dilution of Quizartinib (range from 2.3 nM to 15 µM) as described in the section 1.1.2. Due to increased sensitivity, the range was adjusted for MV(4;11) (0.0015-10 nM) and MOLM-13 cells (0.01-60 nM). Reduction of viability greater than 20% (compared to vehicle controls) was detected in the MV(4;11) ($EC_{50}$<1 nM), OCI-AML2 ($EC_{50}$=830 nM) and MOLM-13 cells ($EC_{50}$<1 nM).

1.2.11.1 Combination ORY-1001/Quizartinib

Figure 9A:
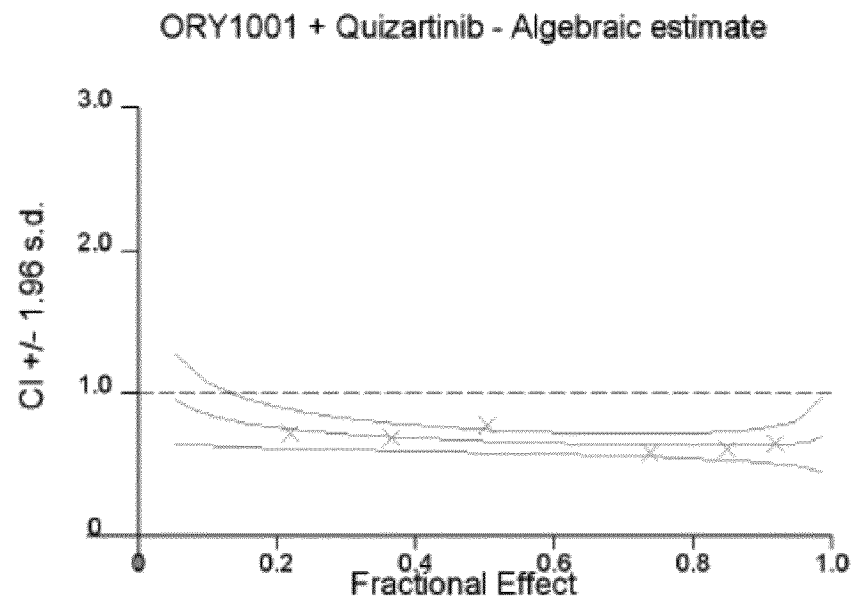
FIG. 9: Combination indexes calculated for the combo ORY-1001/Quizartinib in MV(4;11) (FIG. 9A) and MOLM-13 cells (FIG. 9B) following the procedure described in Example 1.2.11.1.
Figure 9B:
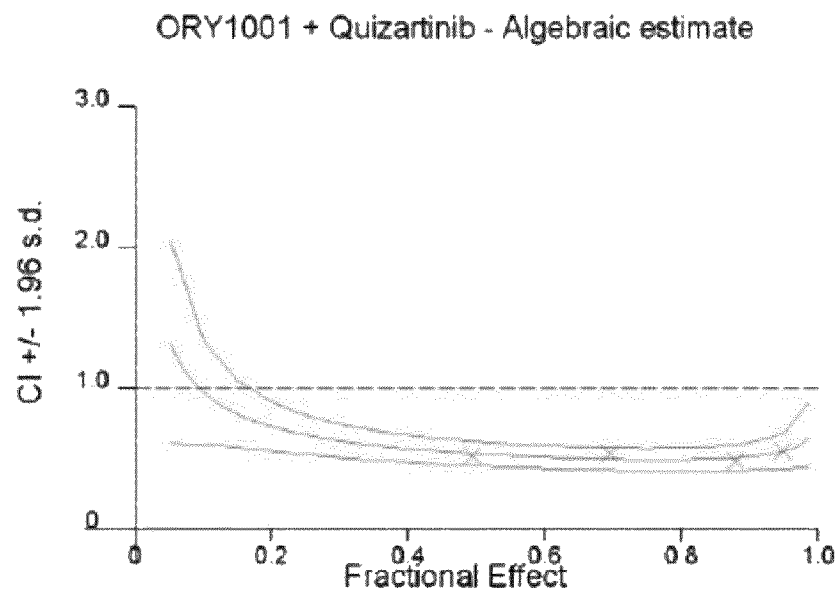

Matrix treatments with Quizartinib (0.031-8 nM) and ORY-1001 (0.006-1.6 nM) were performed on MV(4;11) and MOLM-13 cells as described in the section 1.1.3. Data analysis and calculation of combination indexes as reported in 1.1.3.1. The results obtained are shown in FIGS. 9A and 9B.

In the conditions tested, in MV(4;11) and MOLM-13 cells (both harboring the FLT3-ITD mutation), the combination index for ORY-1001/Quizartinib combo is below 1 (synergistic interaction) at Fa>0.2 (n=2).

1.2.12 ABT737 Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.05%) or serial 1:3 dilution of ABT737 (range from 0.15 nM to 1 µM) as described in the section 1.1.2. Reduction of viability greater than 20% (compared to vehicle controls) was detected in the MV(4;11) ($EC_{50}$=6.3 nM), HL-60 ($EC_{50}$=113.4 nM), OCI-AML2 ($EC_{50}$=14 nM), KASUMI-1 ($EC_{50}$=124 nM) and MOLM-13 cells ($EC_{50}$=25 nM).

1.2.12.1 Combination ORY-1001/ABT737

Figure 10A:
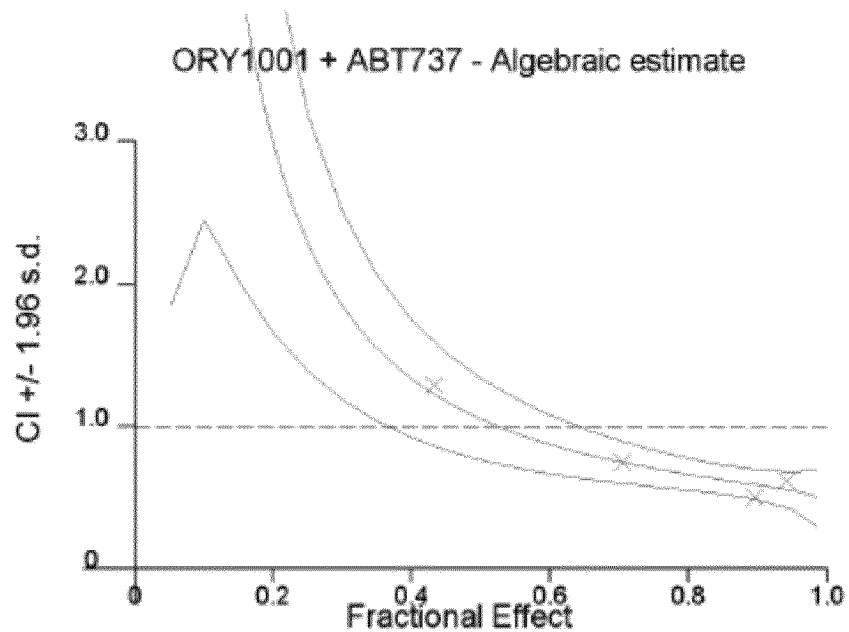
FIG. 10: Combination indexes calculated for the combo ORY1001/ABT737 in MV(4;11) (FIG. 10A) and MOLM-13 cells (FIG. 10B) following the procedure described in Example 1.2.12.1.
Figure 10B:
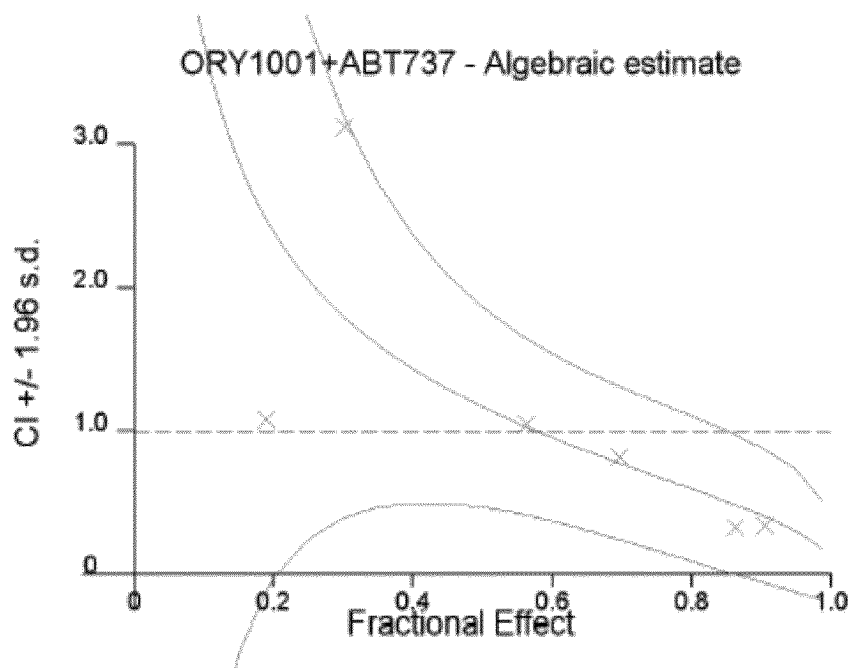

Matrix treatments with ABT373 (0.3-80 nM) and ORY-1001 (0.006-1.6 nM) were performed on MV(4;11) and MOLM-13 cells as described in the section 1.1.3. Data analysis and calculation of combination indexes as reported in 1.1.3.1. The results obtained are shown in FIGS. 10A and 10B.

Synergy between ORY-1001 and ABT737 was detected at Fa>0.7 and Fa>0.9 respectively in MV(4;11) (n=2) and MOLM-13 cells (n=11).

1.2.13 Nutlin3A Single Agent

After determining the optimal growth conditions for the THP-1, MV(4;11), HL-60, OCI-AML3, KASUMI-1, OCI-AML2 and MOLM-13 AML cell lines, incubations were performed with either vehicle (DMSO 0.2%) or serial 1:3 dilution of Nutlin3A (range from 0.6 nM to 4 µM) as described in the section 1.1.2. Reduction of viability greater than 20% (compared to vehicle controls) was detected in the THP-1 ($EC_{50}$=323.7 nM), OCI-AML2 ($EC_{50}$=446.5 nM), OCI-AML3 ($EC_{50}$=659 nM) and MOLM-13 cells ($EC_{50}$=127.7 nM).

1.2.13.1 Combination ORY-1001/Nutlin3A

Figure 11:
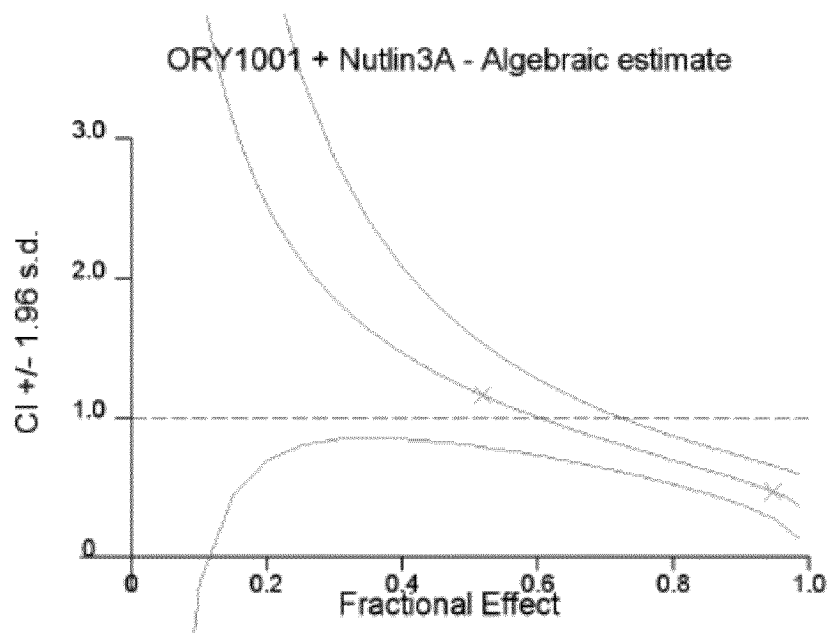
FIG. 11: Combination indexes calculated for the combo ORY1001/Nutlin3A in MOLM-13 cells following the procedure described in Example 1.2.13.1.

Matrix treatments with Nutlin3A (1.1-7290 nM) and ORY-1001 (0.001-8.1 nM) were performed on MOLM-13 cells as described in the section 1.1.3. Data analysis and calculation of combination indexes as reported in 1.1.3.1. The results obtained are shown in FIG. 11.

In the conditions tested, in MOLM-13 cells, ORY-1001 displays synergistic interaction with Nutlin3A for Fa values above 0.8 (n=2).

1.2.14 Combination ORY-1001/Dasatinib

Figure 12:
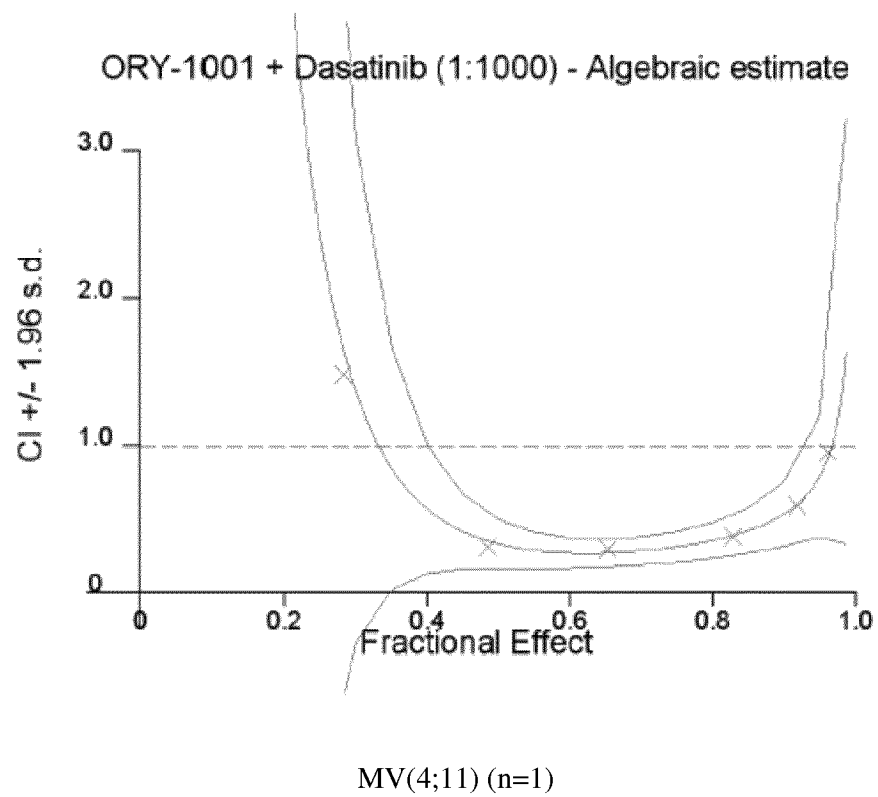
FIG. 12: Combination indexes calculated for the combo ORY1001/Dasatinib in MV(4;11) cells following the procedure described in Example 1.2.14.

Treatment with a combination of Dasatinib (6 nM-40 µM) and ORY-1001 (0.006-40 nM) were performed on MV(4;11) cells as described in the section 1.1.4. Data analysis and calculation of combination indexes as reported in 1.1.4.1. The results obtained are shown in FIG. 12.

In the conditions tested, in MV(4;11) cells, ORY-1001 displays synergistic interaction with Dasatinib for Fa values between 0.4 and 0.9 (n=1).

1.2.15 Combination ORY-1001/JQ1

Figure 13:
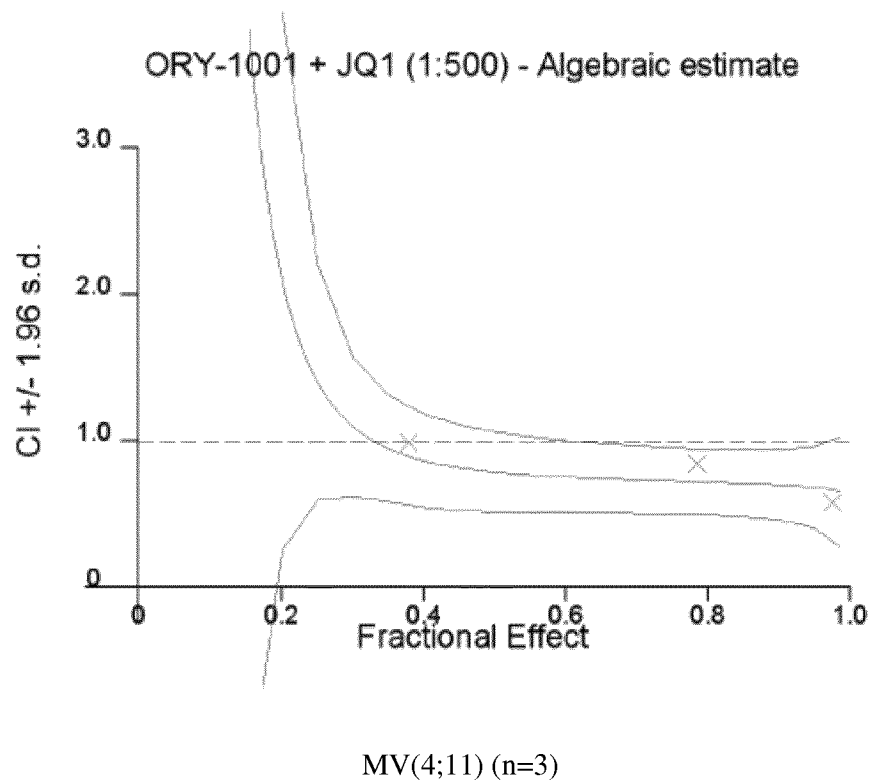
FIG. 13: Combination indexes calculated for the combo ORY1001/JQ1 in MV(4;11) cells following the procedure described in Example 1.2.15.

Treatment with a combination of JQ1 (0.9 nM-6000 nM) and ORY-1001 (0.004-30 nM) were performed on MV(4;11) cells as described in the section 1.1.4. Data analysis and calculation of combination indexes as reported in 1.1.4.1. The results obtained are shown in FIG. 13.

In the conditions tested, in MV(4;11) cells, ORY-1001 displays synergistic interaction with JQ1 for Fa values between 0.6 and 0.9 (n=3).

1.2.16 Combination ORY-1001/Hydroxyurea

Figure 14:
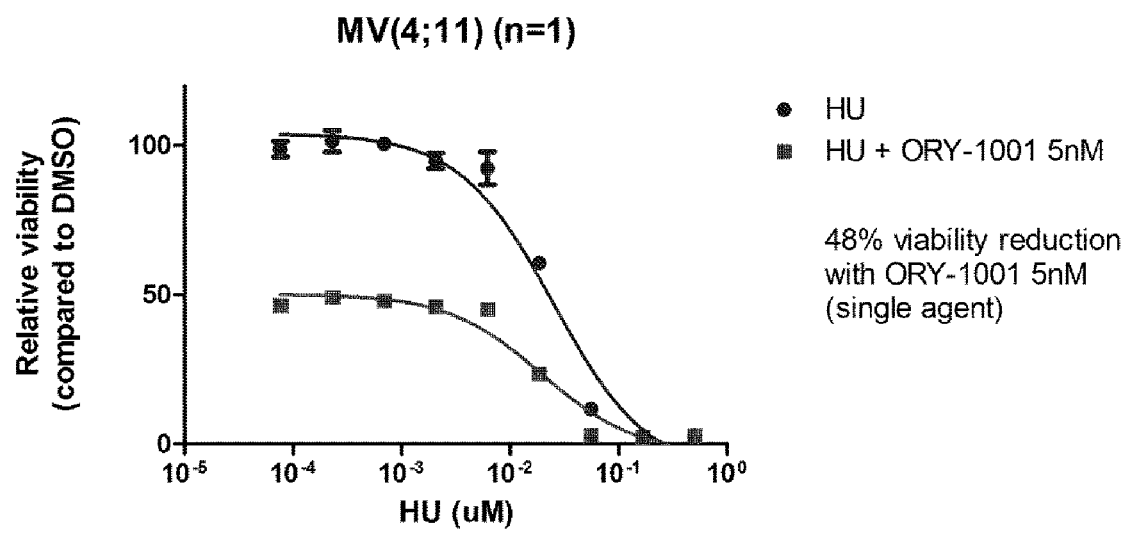
FIG. 14: Dose-response curve of MV(4;11) cells treated with Hydroxyurea (HU) in combination with ORY-1001, following the procedure described in Example 1.2.16.

Treatment with serial dilution of Hydroxyurea (0.076-500 nM) was performed in presence of either ORY-1001 (5 nM) or vehicle (DMSO 0.05%) in MV(4;11) cells, as described in the section 1.1.5. The results obtained are shown in FIG. 14.

In the conditions tested, ORY-1001 potentiates the response of MV(4;11) cells to Hydroxyurea (n=1).

1.2.17 Combination ORY-1001/$As_2O_3$

Figure 15:
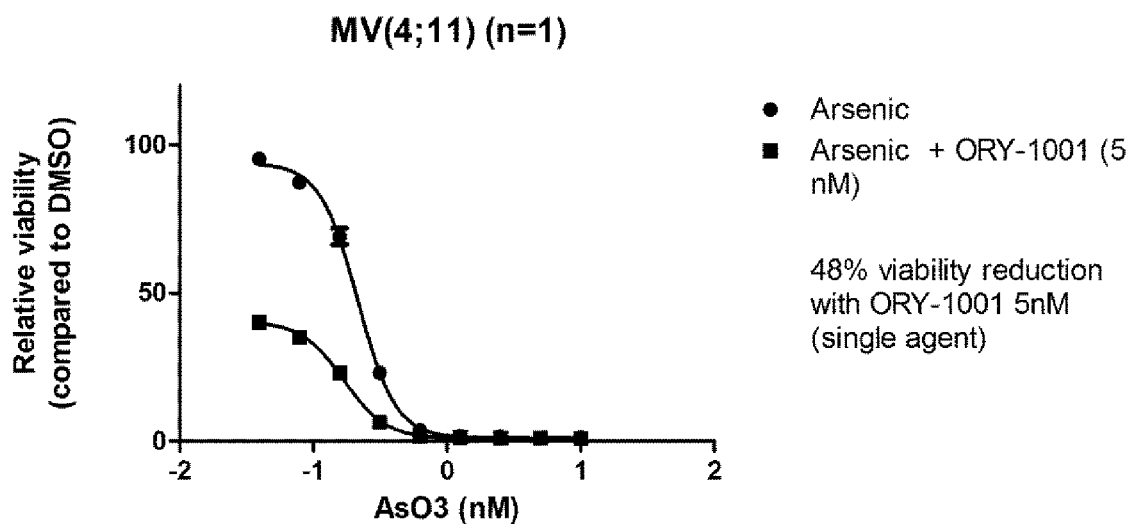
FIG. 15: Dose-response curve of MV(4;11) cells treated with $As_2O_3$(Arsenic) in combination with ORY-1001, following the procedure described in Example 1.2.17.

Treatment with serial dilution of $As_2O_3$ (0.039-10 nM) was performed in presence of either ORY-1001 (5 nM) or vehicle (DMSO 0.05%) in MV(4;11) cells, as described in the section 1.1.6. The results obtained are shown in FIG. 15.

In the conditions tested, ORY-1001 potentiates the response of MV(4;11) cells to $As_2O_3$ (n=1).

Example 2: Matrix Assays for Determination of Synergy Between ORY-1001 and Other Compounds of Interest in MOLT4 Cells (Acute Lymphoid Leukemia)

The objective of this example is to determine synergism existing between ORY-1001 and other therapeutic agents in MOLT4 cells. Table 3 summarizes the compounds tested in the combination therapy and the cell line used.

TABLE 3

List of compounds that will be tested in combination with ORY-1001.

| Compound | Class | Cell lines |
|---|---|---|
| ARAC | Nucleotide analogue | MOLT-4 |
| SAHA | HDAC inhibitor | MOLT-4 |
| Rocilinostat* | HDAC inhibitor | MOLT-4 |
| Entinostat | HDAC inhibitor | MOLT-4 |
| Azacitidine | Demethylating agent | MOLT-4 |
| Decitabine | Demethylating agent | MOLT-4 |
| ABT737 | BCL2 inhibitor | MOLT-4 |

*Also known as Ricolinostat and ACY-1215.

2.1 Experimental Design 2.1.1 Cell Lines and Culture Conditions

MOLT4 cells were maintained in RPMI 10% FBS medium at 37° C. in a humidified incubator with controlled 5% $CO_2$ atmosphere. Cell freezing and thawing was performed following recommendation from ATCC. Genetic profiling of the cell lines used is available in table 4.

TABLE 4

Genetic characterization of the ALL cell line reported in this document.

| Cell lines | Tissue of origin | Mutational status |
|---|---|---|
| MOLT4 | Acute lymphoblastic T-cell leukaemia | MLL wt |

2.1.2 Viability Assays (10 Days)

The effects of ORY-1001 on viability of MOLT-4 cells were evaluated after 10 days of treatment, as a shorter treatment (96 hours) is not affecting the viability of this cell line (data not shown).

MOLT4 cells were seeded at the optimal density, as previously determined (5000 cells/well), in 96-well plates with 50 μL of medium. Three wells were reserved for each experimental condition; medium-only and vehicle-treated controls were also added for background correction and normalization respectively. After seeding, 50 μL of medium containing 8 1:3 serial dilution of ORY-1001 were added to the cells (range 0.015-100 nM). Cells were then incubated for 6 days at 37° C. in a controlled 5% CO2 atmosphere. On the sixth day, 100 μL of medium with serial dilutions of ORY-1001 (as described previously) or vehicle were added to the cells. Medium without compound (100μ) was added to background control.

After 4 additional days of incubation, cell viability was evaluated using the Alamar Blue® staining as detailed in the section 1.1.2.

2.1.3 9×9 Matrix Viability Assays with 100 nM ORY-1001 Pre-Treatment

Each matrix assay was distributed across 2 plates as described in 1.1.3. Matrix assay was adapted according to the observation reported in the section above (2.1.2).

MOLT4 cells were seeded at the optimal density (5000 cells/wells, as previously determined) in 96-well plates with 50 μL of medium. The edges of the plate were filled with 100 μL of medium only, for background correction. For the initial pre-treatment with ORY-1001, 50 μL of medium were added to the cells, resulting in a final volume of 100 μL of medium. Pretreatment of 6 days was performed with a range of ORY-1001 concentrations, obtained through 8 1:2 dilutions steps, designed to have the $EC_{50}$ values for ORY-1001 centered vertically on the matrix. For compounds in which a wider concentration range was tested (Decitabine and Azacitidine) serial dilutions were performed in 1:3 steps. Cells were then incubated for 6 days in a 5% $CO_2$ controlled atmosphere.

On the sixth day, additional 100 μL of medium containing serial dilution of both ORY-1001 and the compound of interest were added to each well (200 μL final volume). As described before, for background correction, 100 μL of medium without cells were also added to the edges of the plate (200 μL final volume). As shown in FIG. 1, the matrix was designed with increasing concentrations of ORY-1001 from left to right and increasing concentrations of the compound of interest from top to the bottom. The first and the last row of plate #1 have been repeated in plate #2 (indicated by red arrows in FIG. 1) to verify reproducibility across the two plates. The concentrations tested for both the compounds were covering a 256-folds range obtained through 8 1:2 dilutions steps, designed to have the $EC_{50}$s of both the compounds centered horizontally and vertically on the matrix (the $EC_{50}$s of ORY-1001 and the other compound correspond to the 5th well from the right and from the bottom, as indicated in FIG. 1). For compounds in which a wide concentration range was tested (Decitabine and Azacitidine Nutlin3A) serial dilutions were performed in 1:3 steps. At this point, cells were incubated for further 96 hours with both the compound.

After 4 days of co-treatment with ORY-1001 and the compound of interest (day 10), Alamar Blue® stock solution was diluted 1:20 in the culture medium and, after 3 hours incubation, fluorescence was detected using a TECAN Infinity 2000 plate reader (Tecan Group Ltd., Männedorf, C H; 540-570 nm excitation wavelength, 580-610 nm emission wavelength). For each condition, background correction was calculated from the fluorescence of medium-only controls. Matrix assays were performed in technical duplicate.

2.1.3.1 9×9 Matrix Viability Assays with 100 nM ORY-1001 Pre-Treatment (Data Analysis)

Data analysis was performed as described in the section 1.1.3.1.

2.1.3.2 Calcusyn Output

Output of the Calcusyn software as described in the section 1.1.3.2.

2.2 Results 2.2.1 ORY-1001 Single Agent

After determining the optimal growth conditions for the MOLT4 cells, incubations were performed with either vehicle (DMSO 0.05%) or serial 1:3 dilution of ORY-1001 (range from 0.015 to 100 nM) as described in the section 2.1.2. In the conditions tested, viability reduction at the highest ORY-1001 concentration (100 nM) was greater than 20% (compared to vehicles), with $EC_{50}$ in the sub-nanomolar range.

2.2.2 Combination ORY-1001/ARA-C

Figure 16:
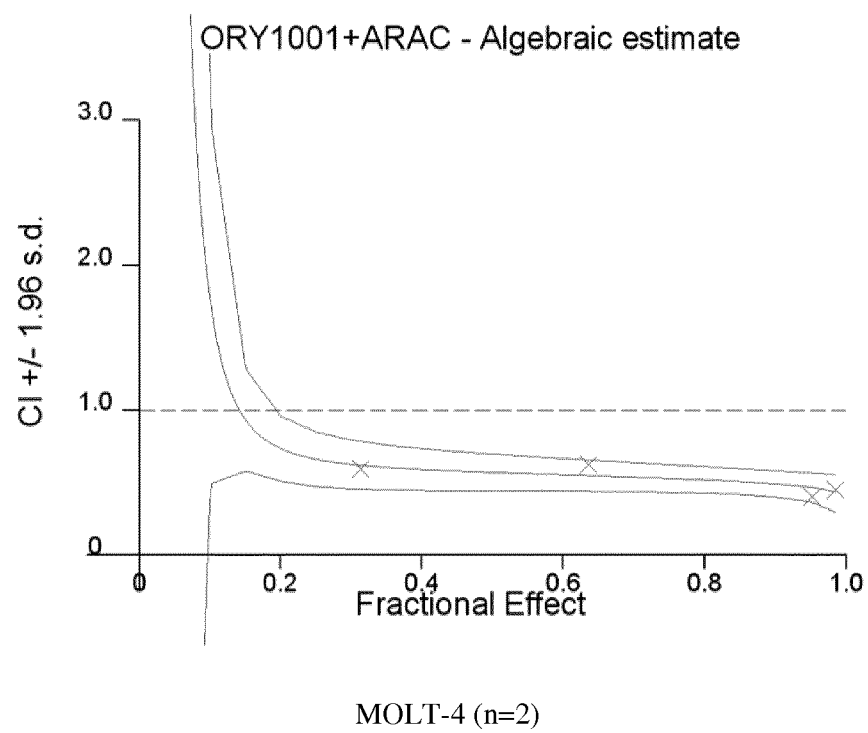
FIG. 16: Combination indexes calculated for the combo ORY-1001/ARA-C in MOLT-4 cells following the procedure described in Example 2.2.2.

Matrix treatment with ARA-C (6.25-1600 nM) and ORY-1001 (0.08-20 nM) was performed on MOLT-4 cells as described in the section 2.1.3. Data analysis and calculation of combination indexes as reported in 2.1.3.1. The results obtained are shown in FIG. 16.

In the conditions tested, In MOLT4 cells, ORY-1001 synergistically enhances the effects of ARAC for Fa values above 0.2 (n=2).

2.2.3 Combination ORY-1001/SAHA

Figure 17:
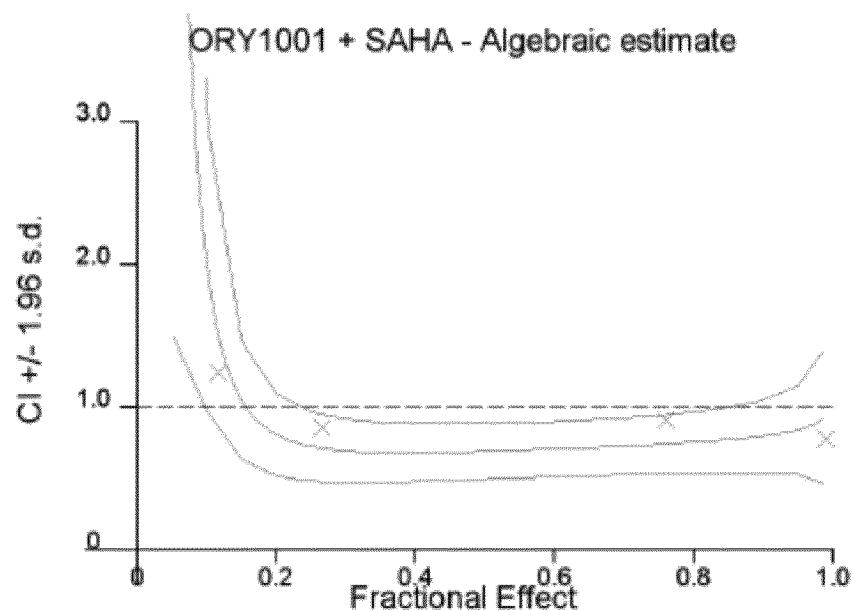
FIG. 17: Combination indexes calculated for the combo ORY-1001/SAHA in MOLT-4 cells following the procedure described in Example 2.2.3.

Matrix treatment with SAHA (12.5-3200 nM) and ORY-1001 (0.08-20 nM) was performed on MOLT-4 cells as described in the section 2.1.3. Data analysis and calculation of combination indexes as reported in 2.1.3.1. The results obtained are shown in FIG. 17.

In the conditions tested, Synergistic interaction between ORY-1001 and SAHA was detected for Fa values comprised between 0.3 and 0.8 (n=2).

2.2.4 Combination ORY-1001/Rocilinostat

Figure 18:
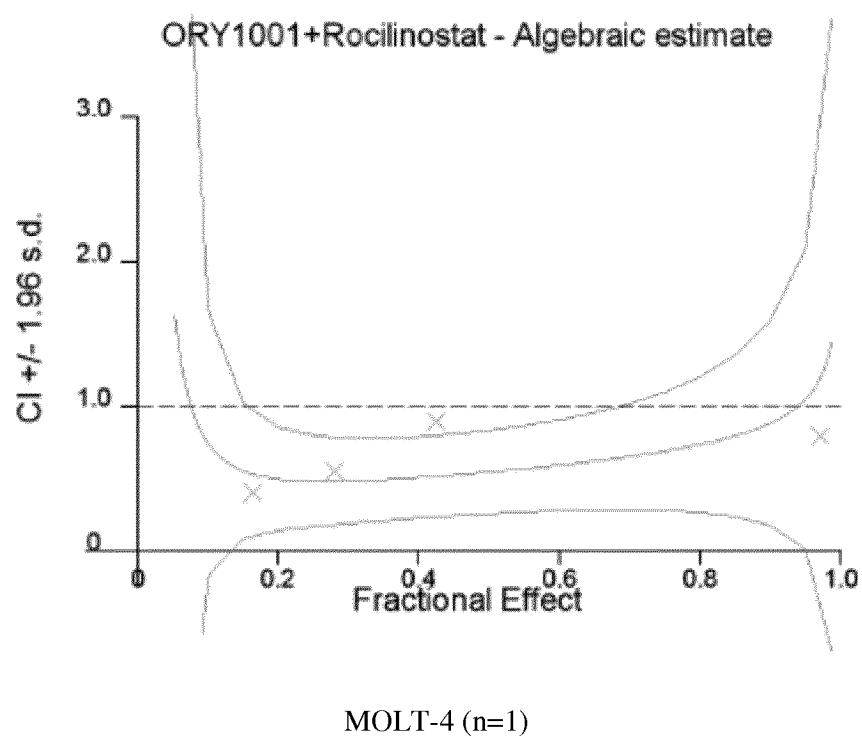
FIG. 18: Combination indexes calculated for the combo ORY1001/Rocilinostat in MOLT-4 cells following the procedure described in Example 2.2.4.

Matrix treatment with Rocilinostat (31.25-8000 nM) and ORY-1001 (0.08-20 nM) was performed on MOLT-4 cells as described in the section 2.1.3. Data analysis and calculation of combination indexes as reported in 2.1.3.1. The results obtained are shown in FIG. 18.

In the conditions tested, as previously observed for SAHA, synergy between ORY-1001 and Rocilinostat was detected for Fa values between 0.2 and 0.6 (n=1).

2.2.5 Combination ORY-1001/Entinostat

Figure 19:
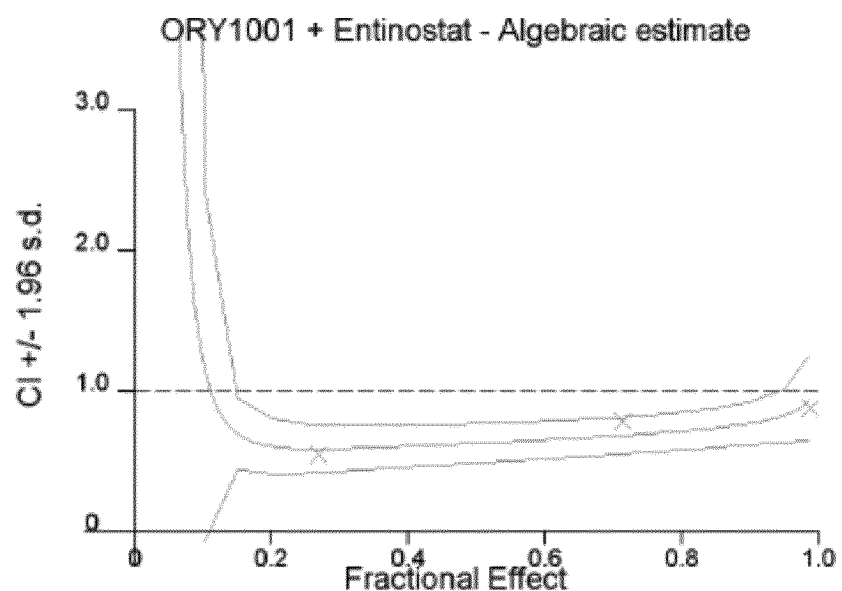
FIG. 19: Combination indexes calculated for the combo ORY-1001/Entinostat in MOLT-4 cells following the procedure described in Example 2.2.5.

Matrix treatment with Entinostat (15.6-4000 nM) and ORY-1001 (0.08-20 nM) was performed on MOLT-4 cells as described in the section 2.1.3. Data analysis and calculation of combination indexes as reported in 2.1.3.1. The results obtained are shown in FIG. 19.

In the conditions tested, as previously observed for SAHA, synergy between ORY-1001 and Entinostat was detected for Fa values between 0.2 and 0.9 (n=2).

2.2.6 Combination ORY-1001/Azacitidine

Figure 20:
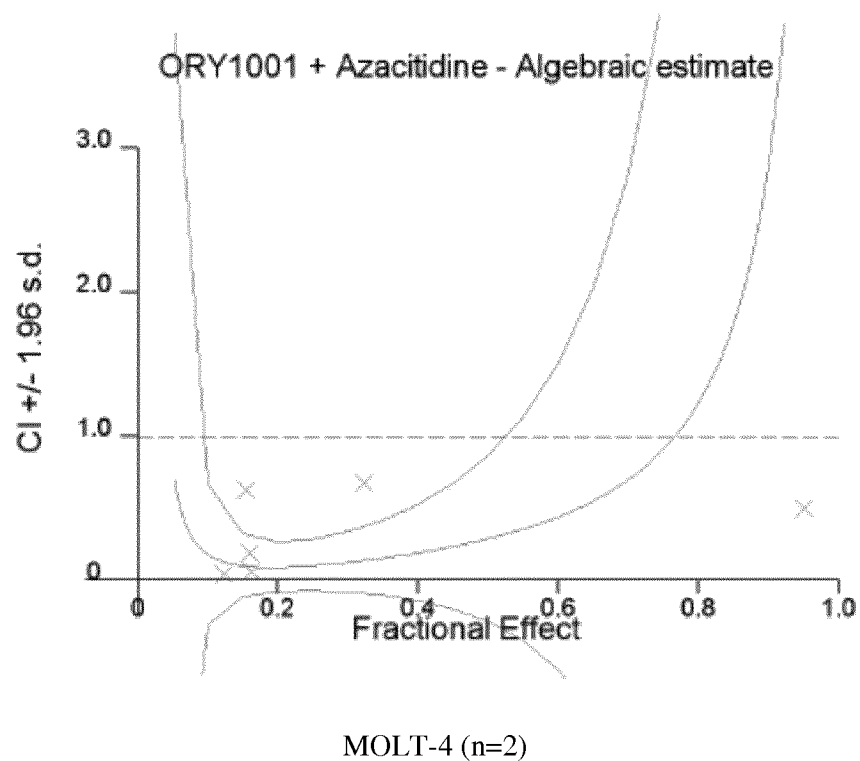
FIG. 20: Combination indexes calculated for the combo ORY-1001/Azacitidine in MOLT-4 cells following the procedure described in Example 2.2.6.

Matrix treatment with Azacitidine (13.72 nM-90 µM) and ORY-1001 (0.012-81 nM) was performed on MOLT-4 cells as described in the section 2.1.3. Data analysis and calculation of combination indexes as reported in 2.1.3.1. The results obtained are shown in FIG. 20.

In the conditions tested, synergy between Azacitidine and ORY-1001 was detected only in the narrow range of Fa valued between 0.2 and 0.4 (n=2).

2.2.7 Combination ORY-1001/Decitabine

Figure 21:
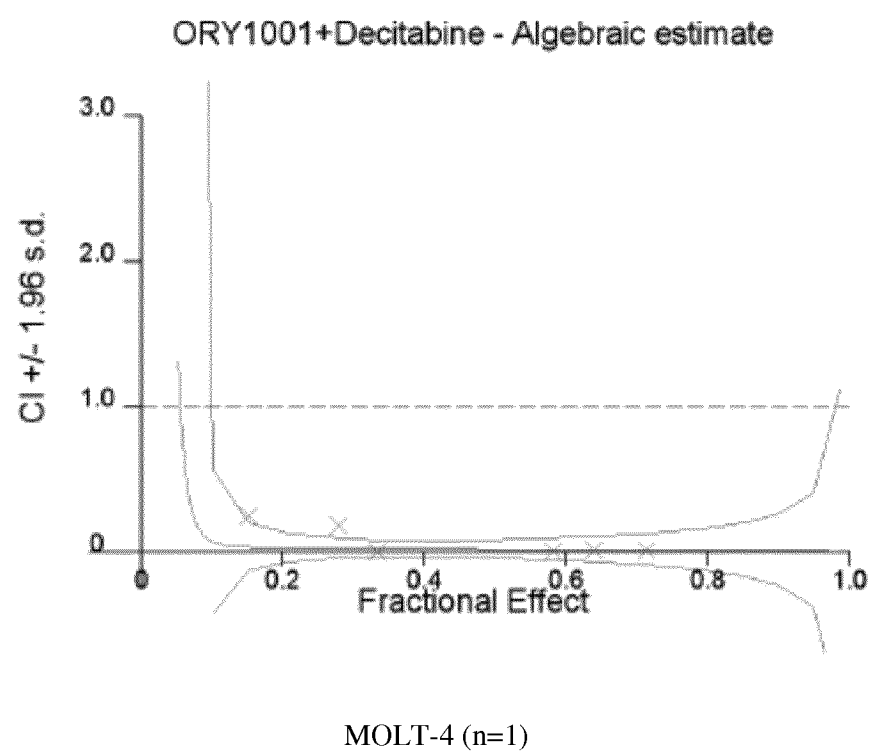
FIG. 21: Combination indexes calculated for the combo ORY-1001/Decitabine in MOLT-4 cells following the procedure described in Example 2.2.7.

Matrix treatment with Decitabine (1.5 nM-10 µM) and ORY-1001 (0.012-81 nM) was performed on MOLT-4 cells as described in the section 2.1.3. Data analysis and calculation of combination indexes as reported in 2.1.3.1. The results obtained are shown in FIG. 21.

In the conditions tested, Decitabine strongly synergizes with ORY-1001 within a wide range of Fa values (Fa values between 0.1 and 0.9; n=1).

2.2.8 Combination ORY-1001/ABT737

Figure 22:
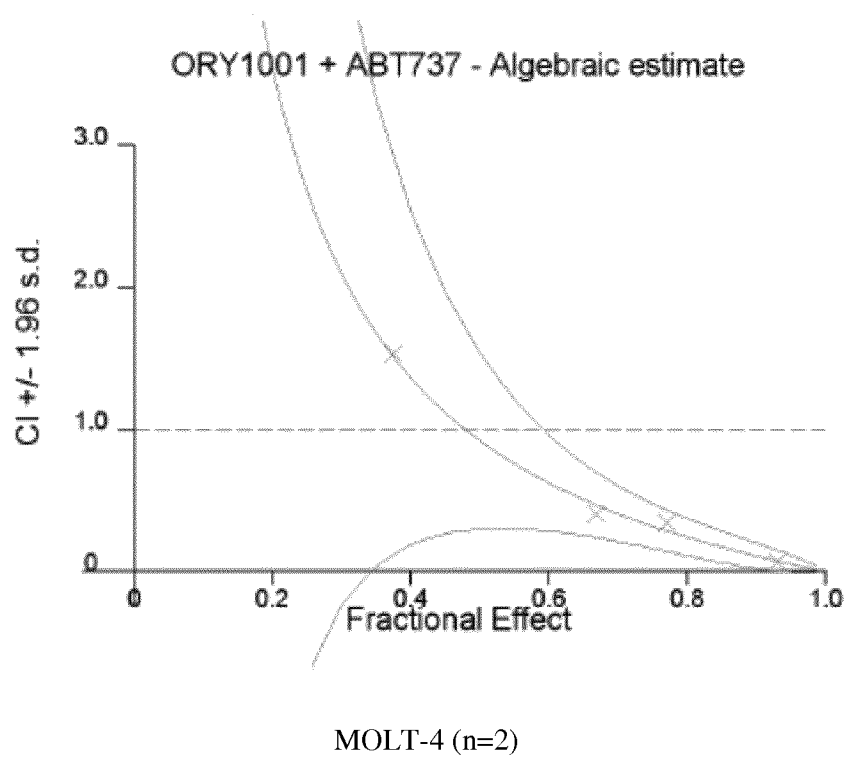
FIG. 22: Combination indexes calculated for the combo ORY1001/ABT737 in MOLT-4 cells following the procedure described in Example 2.2.8.

Matrix treatment with ABT737 (19.53-5000 nM) and ORY-1001 (0.08-20 nM) was performed on MOLT-4 cells as described in the section 2.1.3. Data analysis and calculation of combination indexes as reported in 2.1.3.1. The results obtained are shown in FIG. 22.

In the conditions tested, in MOLT4 cells, synergy between ORY-1001 and ABT737 was detected for Fa values greater than 0.6 (n=2).

[1] Shi et al. (2004) Cell 119:941
[2] WO 2013/057322 A1
[3] U.S. Pat. No. 2,709,712 A
[4] WHO Chronicle, Vol. 25, No. 10, 1971
[5] Chu M. Y. et al. Biochemical Pharmacology (1962) 11:423-30
[6] WHO Chronicle, Vol. 20, No. 11, 1966
[7] WO 2012/075381 A1
[8] WHO Drug Information, Vol. 28, No. 4, 2014
[9] Daigle S. R. et al. Cancer Cell (2011) 20(1):53-65
[10] Yu et al., Nature Communications (2012) 3(1288):1-11
[11] WO 93/07148 A1
[12] WHO Drug Information, Vol. 20, No. 3, 2006
[13] WO 2011/091213 A2
[14] WHO Drug Information, Vol. 28, No. 1, 2014
[15] JP 10152462 A
[16] WHO Drug Information, Vol. 23, No. 1, 2009
[17] WO 2009/040517 A2
[18] WO 02/022577 A2
[19] G Huis et al., 2015, Blood Journal, 126(3):283-284, DOI: http://dx.doi.org/10.1182/blood-2015-06-648071
[20] Wolfrom I. M. L. et al. Journal of Organic Chemistry (1964) 29(11):3280-3283
[21] WHO Drug Information, Vol. 4, No. 3, 1990
[22] DE 1140941 BI
[23] Supplement to WHO Chronicle, Vol. 33, No. 10, 1979
[24] WO 2007/109120 A2
[25] WHO Drug Information, Vol. 25, No. 3, 2011
[26] WO 2005/049594 A1
[27] US 2007/0027135 A1
[28] WO 2004/106328 A1
[29] WO 2010/138588 A2
[30] US 2005/0282803 A1
[31] WO 2011/143651 A1
[32] WO 2011/054843 A1
[33] WO 2012/116170 A1
[34] U.S. Pat. No. 5,712,274 A
[35] WO 2014/134583 A2
[36] WO 2011/054843 A1
[37] S. P. Parker, Ed., McGraw-Hill Dictionary of Chemical Terms (1984) McGraw-Hill Book Company, New York
[38] Eliel, E. and Wilen, S., "Stereochemistry of Organic Compounds", John Wiley & Sons, Inc., New York, 1994
[39] Cahn et al. Angew. Chem. Inter. Edit. 1966, 5, 385; errata 511
[40] Ansel's Pharmaceutical Dosage Forms and Drug Delivery Systems (2004) Lippincott, Williams & Wilkins, Philadelphia
[41] Remington: The Science and Practice of Pharmacy (2000) Lippincott, Williams & Wilkins, Philadelphia
[42] Handbook of Pharmaceutical Excipients (2005) Pharmaceutical Press, Chicago
[43] Al-Nasiry et al. (2007) Hum Reprod 22:1304-1309
[44] T. C. Chou, Pharmacol Rev. 2006
[45] T. C. Chou and P. Talalay, Trends Pharmacol. Sci. 2006
[46] T. C. Chou, Cancer Research 2010

The invention claimed is:

1. A combination comprising a compound of formula (I):

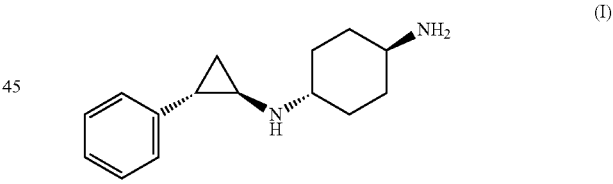

or a pharmaceutically acceptable salt thereof, and one or more therapeutic agents selected from decitabine, azacitidine, and pharmaceutically acceptable salts thereof.

2. The combination according to claim 1 comprising a compound of formula (I):

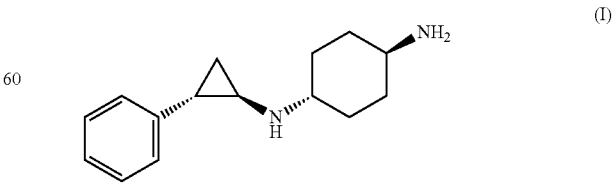

or a pharmaceutically acceptable salt thereof, and azacitidine or a pharmaceutically acceptable salt thereof.

3. The combination according to claim 1 comprising a compound of formula (I):

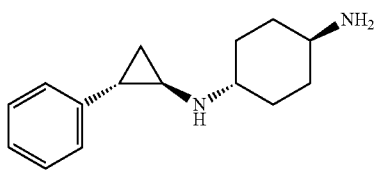
(I)

or a pharmaceutically acceptable salt thereof, and decitabine, or a pharmaceutically acceptable salt thereof.

4. A pharmaceutical composition comprising a combination according to claim 1 and one or more pharmaceutically acceptable excipients.

5. A method for the treatment of a hematological malignancy in a patient in need thereof, which method comprises administering a therapeutically effective amount of a combination according to claim 1 to said patient.

6. A method for the treatment of a hematological malignancy in a patient in need thereof, which method comprises administering the pharmaceutical composition according to claim 4 to said patient.

7. The method of claim 5 wherein the hematological malignancy is a myeloid hematological malignancy.

8. The method of claim 7, wherein the myeloid hematological malignancy is acute myeloid leukemia, chronic myelogenus leukemia, myelodysplastic syndrome or a myeloproliferative disease.

9. The method of claim 5 wherein the hematological malignancy is a lymphoid hematological malignancy.

10. The method of claim 9, wherein the lymphoid hematological malignancy is acute lymphoblastic leukemia.

11. The method of claim 5, wherein the patient is a human being.

12. The combination according to claim 1 comprising a compound of formula (I):

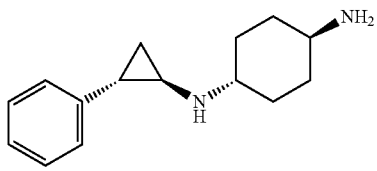
(I)

or a pharmaceutically acceptable salt thereof, and azacitidine or decitabine.

13. The combination according to claim 2 comprising a compound of formula (I):

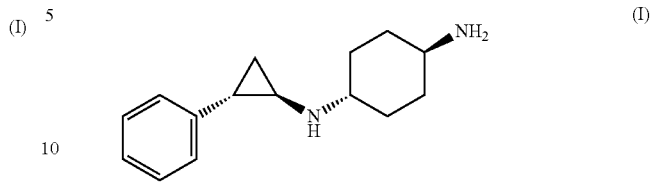
(I)

or a pharmaceutically acceptable salt thereof, and azacitidine.

14. The combination according to claim 2 comprising a dihydrochloride salt of the compound of formula (I):

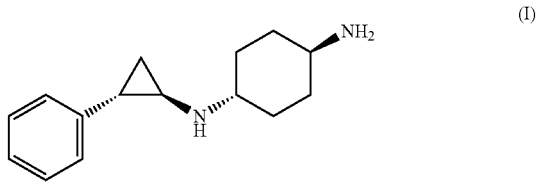 [SMILES: N[C@H]1CC[C@H](N[C@@H]2C[C@H]2c2ccccc2)CC1]
(I)

and azacitidine.

15. The combination according to claim 3 comprising a compound of formula (I):

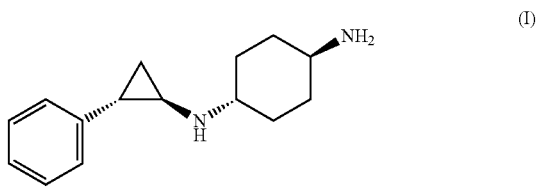 [SMILES: N[C@H]1CC[C@H](N[C@@H]2C[C@H]2c2ccccc2)CC1]
(I)

or a pharmaceutically acceptable salt thereof, and decitabine.

16. The combination according to claim 3 comprising a dihydrochloride salt of the compound of formula (I):

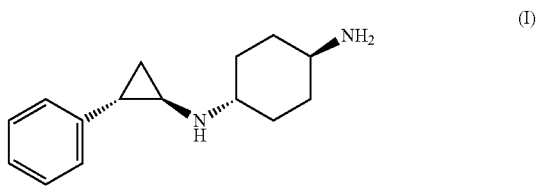 [SMILES: N[C@H]1CC[C@H](N[C@@H]2C[C@H]2c2ccccc2)CC1]
(I)

and decitabine.

17. A pharmaceutical composition comprising a combination according to claim 2 and one or more pharmaceutically acceptable excipients.

18. A pharmaceutical composition comprising a combination according to claim 3 and one or more pharmaceutically acceptable excipients.

* * * * *